(12) United States Patent
Sharma

(10) Patent No.: US 9,700,365 B2
(45) Date of Patent: *Jul. 11, 2017

(54) METHOD AND APPARATUS FOR THE ABLATION OF GASTROINTESTINAL TISSUE

(75) Inventor: Virender K. Sharma, Paradise Valley, AZ (US)

(73) Assignee: Santa Anna Tech LLC, Santa Ana, CA (US)

( * ) Notice: Subject to any disclaimer, the term of this patent is extended or adjusted under 35 U.S.C. 154(b) by 990 days.

This patent is subject to a terminal disclaimer.

(21) Appl. No.: 12/573,946

(22) Filed: Oct. 6, 2009

(65) Prior Publication Data

US 2010/0114083 A1    May 6, 2010

Related U.S. Application Data

(60) Provisional application No. 61/102,885, filed on Oct. 6, 2008.

(51) Int. Cl.
*A61B 18/04* (2006.01)
*A61B 18/00* (2006.01)
(Continued)

(52) U.S. Cl.
CPC ............ *A61B 18/04* (2013.01); *A61B 5/1076* (2013.01); *A61B 17/24* (2013.01); *A61B 2017/00084* (2013.01); *A61B 2018/00488* (2013.01); *A61B 2018/00577* (2013.01); *A61B 2018/00642* (2013.01); *A61B 2018/00773* (2013.01);
(Continued)

(58) Field of Classification Search
CPC A61B 2018/00488; A61B 2018/00285; A61B 2018/00071; A61B 2018/00773; A61B 2018/00642; A61B 2018/00577; A61B 18/04; A61B 5/1076; A61M 25/1011
USPC .............. 606/27, 31, 45–46; 604/509, 94.01, 604/101.01, 101.03, 101.05, 103.14
See application file for complete search history.

(56) References Cited

U.S. PATENT DOCUMENTS

| 408,899 A | 8/1889 | Small |
| 697,181 A | 4/1902 | Smith |

(Continued)

FOREIGN PATENT DOCUMENTS

| FR | 2655548 | 6/1991 |
| WO | 9210142 | 6/1992 |

(Continued)

OTHER PUBLICATIONS

"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/cpu.aspx>.

(Continued)

*Primary Examiner* — Jaymi Della
(74) *Attorney, Agent, or Firm* — Novel IP

(57) ABSTRACT

The present invention is directed toward a device that performs ablation of tissue. The device has a catheter with a shaft through which an ablative agent can travel, a first positioning element attached to the catheter shaft at a first position and a second positioning element attached to the catheter shaft at a second position. The shaft also has ports through which the ablative agent can be released.

14 Claims, 17 Drawing Sheets

(51) Int. Cl.
  A61B 5/107 (2006.01)
  A61B 17/24 (2006.01)
  A61B 17/00 (2006.01)
  A61M 25/10 (2013.01)
(52) U.S. Cl.
  CPC .............. A61B 2018/00791 (2013.01); A61B 2018/048 (2013.01); A61M 25/1011 (2013.01); A61M 2205/3368 (2013.01)

(56) References Cited

U.S. PATENT DOCUMENTS

| | | | |
|---|---|---|---|
| 1,719,750 | A | 7/1929 | Bridge |
| 3,818,913 | A | 6/1974 | Wallach |
| 3,880,168 | A | 4/1975 | Berman |
| 3,924,628 | A | 12/1975 | Droegemueller |
| 3,930,505 | A | 1/1976 | Wallach |
| 3,938,502 | A | 2/1976 | Bom |
| 4,024,866 | A | 5/1977 | Wallach |
| 4,083,077 | A | 4/1978 | Knight |
| 4,672,962 | A | 6/1987 | Hershenson |
| 4,672,963 | A | 6/1987 | Barken |
| 4,682,596 | A | 7/1987 | Bales |
| 4,701,587 | A | 10/1987 | Carter |
| 4,748,979 | A | 6/1988 | Hershenson |
| 4,773,410 | A | 9/1988 | Blackmer |
| 4,793,352 | A | 12/1988 | Eichenlaub |
| 4,872,920 | A | 10/1989 | Flynn |
| 4,898,574 | A | 2/1990 | Uchiyama |
| 4,915,113 | A | 4/1990 | Holman |
| 4,950,266 | A | 8/1990 | Sinofsky |
| 4,950,267 | A | 8/1990 | Ishihara |
| 4,976,711 | A | 12/1990 | Parins |
| 4,985,027 | A | 1/1991 | Dressel |
| 5,006,119 | A | 4/1991 | Acker |
| 5,011,566 | A | 4/1991 | Hoffman |
| 5,045,056 | A | 9/1991 | Behl |
| 5,084,043 | A | 1/1992 | Hertzmann |
| 5,084,044 | A | 1/1992 | Quint |
| 5,102,410 | A | 4/1992 | Dressel |
| 5,112,328 | A | 5/1992 | Taboada |
| 5,122,138 | A | 6/1992 | Manwaring |
| 5,158,536 | A | 10/1992 | Sekins |
| 5,190,539 | A | 3/1993 | Fletcher |
| 5,217,459 | A | 6/1993 | Kamerling |
| 5,217,465 | A | 6/1993 | Steppe |
| 5,222,938 | A | 6/1993 | Behl |
| 5,263,951 | A | 11/1993 | Spears |
| 5,277,696 | A | 1/1994 | Hagen |
| 5,298,298 | A | 3/1994 | Hoffman |
| 5,312,399 | A | 5/1994 | Hakky |
| 5,318,014 | A | 6/1994 | Carter |
| 5,330,518 | A | 7/1994 | Neilson |
| 5,331,947 | A | 7/1994 | Shturman |
| 5,334,190 | A | 8/1994 | Seiler |
| 5,344,397 | A | 9/1994 | Heaven |
| 5,348,551 | A | 9/1994 | Spears |
| 5,352,512 | A | 10/1994 | Hoffman |
| 5,366,490 | A | 11/1994 | Edwards |
| 5,370,609 | A | 12/1994 | Drasler |
| 5,370,675 | A | 12/1994 | Edwards |
| 5,385,544 | A | 1/1995 | Edwards |
| 5,405,376 | A | 4/1995 | Mulier |
| 5,409,453 | A | 4/1995 | Lundquist |
| 5,417,686 | A | 5/1995 | Peterson |
| 5,421,819 | A | 6/1995 | Edwards |
| 5,424,620 | A | 6/1995 | Cheon |
| 5,433,708 | A | 7/1995 | Nichols |
| 5,433,739 | A | 7/1995 | Sluijter |
| 5,435,805 | A | 7/1995 | Edwards |
| 5,437,629 | A | 8/1995 | Goldrath |
| 5,443,470 | A | 8/1995 | Stern |
| 5,449,380 | A | 9/1995 | Chin |
| 5,451,208 | A | 9/1995 | Goldrath |
| 5,462,521 | A | 10/1995 | Brucker |
| 5,470,308 | A | 11/1995 | Edwards |
| 5,470,309 | A | 11/1995 | Edwards |
| 5,484,400 | A | 1/1996 | Edwards |
| 5,500,012 | A | 3/1996 | Brucker |
| 5,503,638 | A | 4/1996 | Cooper |
| 5,524,620 | A | 6/1996 | Rosenschein |
| 5,529,076 | A | 6/1996 | Schachar |
| 5,531,676 | A | 7/1996 | Edwards |
| 5,540,658 | A | 7/1996 | Evans |
| 5,542,915 | A | 8/1996 | Edwards |
| 5,542,916 | A | 8/1996 | Hirsch |
| 5,542,928 | A | 8/1996 | Evans |
| 5,545,171 | A | 8/1996 | Sharkey |
| 5,549,628 | A | 8/1996 | Cooper |
| 5,549,644 | A | 8/1996 | Lundquist |
| 5,554,110 | A | 9/1996 | Edwards |
| 5,554,172 | A | 9/1996 | Horner |
| 5,556,377 | A | 9/1996 | Rosen |
| 5,558,673 | A | 9/1996 | Edwards |
| 5,562,608 | A | 10/1996 | Sekins |
| 5,575,803 | A | 11/1996 | Cooper |
| 5,584,872 | A | 12/1996 | LaFontaine |
| 5,588,960 | A | 12/1996 | Edwards |
| 5,591,125 | A | 1/1997 | Edwards |
| 5,591,157 | A | 1/1997 | Hennings |
| 5,591,162 | A | 1/1997 | Fletcher |
| 5,599,294 | A | 2/1997 | Edwards |
| 5,601,591 | A | 2/1997 | Edwards |
| 5,616,120 | A | 4/1997 | Andrew |
| 5,620,440 | A | 4/1997 | Heckele |
| 5,624,392 | A | 4/1997 | Saab |
| 5,630,794 | A | 5/1997 | Lax |
| 5,667,488 | A | 9/1997 | Lundquist |
| 5,669,907 | A | 9/1997 | Platt, Jr. |
| 5,672,153 | A | 9/1997 | Lax |
| 5,672,290 | A | 9/1997 | Levy |
| 5,674,191 | A | 10/1997 | Edwards |
| 5,681,282 | A | 10/1997 | Eggers |
| 5,683,366 | A | 11/1997 | Eggers |
| 5,695,507 | A | 12/1997 | Auth |
| 5,697,281 | A | 12/1997 | Eggers |
| 5,697,536 | A | 12/1997 | Eggers |
| 5,697,882 | A | 12/1997 | Eggers |
| 5,697,909 | A | 12/1997 | Eggers |
| 5,700,262 | A | 12/1997 | Acosta |
| 5,707,352 | A | 1/1998 | Sekins |
| 5,720,718 | A | 2/1998 | Rosen |
| 5,720,719 | A | 2/1998 | Edwards |
| 5,730,719 | A | 3/1998 | Edwards |
| 5,735,811 | A | 4/1998 | Brisken |
| 5,741,247 | A | 4/1998 | Rizoiu |
| 5,741,248 | A | 4/1998 | Stern |
| 5,743,870 | A | 4/1998 | Edwards |
| 5,752,965 | A | 5/1998 | Francis |
| 5,755,753 | A | 5/1998 | Knowlton |
| 5,769,880 | A | 6/1998 | Truckai |
| 5,782,914 | A | 7/1998 | Schankereli |
| 5,785,521 | A | 7/1998 | Rizoiu |
| 5,797,903 | A | 8/1998 | Swanson |
| 5,800,379 | A | 9/1998 | Edwards |
| 5,800,482 | A | 9/1998 | Pomeranz |
| 5,800,493 | A | 9/1998 | Stevens |
| 5,810,764 | A | 9/1998 | Eggers |
| 5,820,580 | A | 10/1998 | Edwards |
| 5,824,703 | A | 10/1998 | Clark, Jr. |
| 5,827,268 | A | 10/1998 | Laufer |
| 5,830,179 | A | 11/1998 | Mikus |
| 5,836,906 | A | 11/1998 | Edwards |
| 5,843,019 | A | 12/1998 | Eggers |
| 5,843,073 | A | 12/1998 | Sinofsky |
| 5,849,011 | A | 12/1998 | Jones |
| 5,871,469 | A | 2/1999 | Eggers |
| 5,871,481 | A | 2/1999 | Kannenberg |
| 5,873,855 | A | 2/1999 | Eggers |
| 5,873,877 | A | 2/1999 | McGaffigan |
| 5,879,329 | A | 3/1999 | Ginsburg |
| 5,885,243 | A | 3/1999 | Capetan |
| 5,888,198 | A | 3/1999 | Eggers |
| 5,891,095 | A | 4/1999 | Eggers |

(56) References Cited

U.S. PATENT DOCUMENTS

| | | |
|---|---|---|
| 5,891,134 A | 4/1999 | Goble |
| 5,891,457 A | 4/1999 | Neuwirth |
| 5,902,272 A | 5/1999 | Eggers |
| 5,913,856 A | 6/1999 | Chia |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | McGaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Argiro |
| 5,989,212 A | 11/1999 | Sussman |
| 5,989,238 A | 11/1999 | Ginsburg |
| 5,989,249 A | 11/1999 | Kirwan, Jr. |
| 5,989,445 A | 11/1999 | Wise |
| 5,997,499 A | 12/1999 | Sussman |
| 6,015,406 A | 1/2000 | Goble |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,066,132 A | 5/2000 | Chen |
| 6,066,134 A | 5/2000 | Eggers |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | LaFleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |
| 6,126,682 A | 10/2000 | Sharkey |
| 6,130,671 A | 10/2000 | Argiro |
| 6,139,571 A | 10/2000 | Fuller |
| 6,149,620 A | 11/2000 | Baker |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | LaFontaine |
| 6,174,308 B1 | 1/2001 | Goble |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,238,389 B1 | 5/2001 | Paddock |
| 6,238,391 B1 | 5/2001 | Olsen |
| 6,241,702 B1 | 6/2001 | Lundquist |
| 6,254,597 B1 | 7/2001 | Rizoiu |
| 6,254,600 B1 | 7/2001 | Willink |
| 6,258,087 B1 | 7/2001 | Edwards |
| 6,261,286 B1 | 7/2001 | Goble |
| 6,261,311 B1 | 7/2001 | Sharkey |
| 6,264,650 B1 | 7/2001 | Hovda |
| 6,264,651 B1 | 7/2001 | Underwood |
| 6,264,652 B1 | 7/2001 | Eggers |
| 6,264,654 B1 | 7/2001 | Swartz |
| 6,277,112 B1 | 8/2001 | Underwood |
| 6,277,114 B1 | 8/2001 | Bullivant |
| 6,283,961 B1 | 9/2001 | Underwood |
| 6,283,989 B1 | 9/2001 | Laufer |
| 6,287,274 B1 | 9/2001 | Sussman |
| 6,287,320 B1 | 9/2001 | Slepian |
| 6,290,715 B1 | 9/2001 | Sharkey |
| 6,293,942 B1 | 9/2001 | Goble |
| 6,296,636 B1 | 10/2001 | Cheng |
| 6,296,638 B1 | 10/2001 | Davison |
| 6,299,633 B1 | 10/2001 | Laufer |
| 6,300,150 B1 | 10/2001 | Venkatasubramanian |
| 6,306,129 B1 | 10/2001 | Little |
| 6,306,134 B1 | 10/2001 | Goble |
| 6,309,387 B1 | 10/2001 | Eggers |
| 6,312,408 B1 | 11/2001 | Eggers |
| 6,312,474 B1 | 11/2001 | Francis |
| 6,315,755 B1 | 11/2001 | Sussman |
| 6,319,222 B1 | 11/2001 | Andrew |
| 6,322,549 B1 | 11/2001 | Eggers |
| 6,327,505 B1 | 12/2001 | Medhkour |
| 6,331,171 B1 | 12/2001 | Cohen |
| 6,355,032 B1 | 3/2002 | Hovda |
| 6,363,937 B1 | 4/2002 | Hovda |
| 6,364,877 B1 | 4/2002 | Goble |
| 6,375,635 B1 | 4/2002 | Moutafis |
| 6,379,350 B1 | 4/2002 | Sharkey |
| 6,379,351 B1 | 4/2002 | Thapliyal |
| 6,391,025 B1 | 5/2002 | Weinstein |
| 6,394,949 B1 | 5/2002 | Crowley |
| 6,394,996 B1 | 5/2002 | Lawrence |
| 6,398,759 B1 | 6/2002 | Sussman |
| 6,398,775 B1 | 6/2002 | Perkins |
| 6,409,723 B1 | 6/2002 | Edwards |
| 6,416,507 B1 | 7/2002 | Eggers |
| 6,416,508 B1 | 7/2002 | Eggers |
| 6,416,509 B1 | 7/2002 | Goble |
| 6,423,027 B1 | 7/2002 | Gonon |
| 6,432,103 B1 | 8/2002 | Ellsberry |
| 6,440,127 B2 | 8/2002 | McGovern |
| 6,458,231 B1 | 10/2002 | Wapner |
| 6,461,350 B1 | 10/2002 | Underwood |
| 6,461,354 B1 | 10/2002 | Olsen |
| 6,464,694 B1 | 10/2002 | Massengill |
| 6,464,695 B2 | 10/2002 | Hovda |
| 6,468,270 B1 | 10/2002 | Hovda |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |

(56) References Cited

U.S. PATENT DOCUMENTS

| | | |
|---|---|---|
| 6,493,589 B1 | 12/2002 | Medhkour |
| 6,500,173 B2 | 12/2002 | Underwood |
| 6,508,816 B2 | 1/2003 | Shadduck |
| 6,510,854 B2 | 1/2003 | Goble |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |
| 6,551,274 B2 | 4/2003 | Heiner |
| 6,551,300 B1 | 4/2003 | McGaffigan |
| 6,557,559 B1 | 5/2003 | Eggers |
| 6,558,314 B1 | 5/2003 | Adelman |
| 6,558,379 B1 | 5/2003 | Batchelor |
| 6,566,636 B1 | 5/2003 | Bentley |
| 6,569,146 B1 | 5/2003 | Werner |
| 6,575,929 B2 | 6/2003 | Sussman |
| 6,575,932 B1 | 6/2003 | OBrien |
| 6,575,968 B1 | 6/2003 | Eggers |
| 6,579,270 B2 | 6/2003 | Sussman |
| 6,582,423 B1 | 6/2003 | Thapliyal |
| 6,585,639 B1 | 7/2003 | Kotmel |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,087 B2 | 8/2003 | Swartz |
| 6,607,529 B1 | 8/2003 | Jones |
| 6,610,043 B1 | 8/2003 | Ingenito |
| 6,620,130 B1 | 9/2003 | Ginsburg |
| 6,620,155 B2 | 9/2003 | Underwood |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,648,847 B2 | 11/2003 | Sussman |
| 6,652,594 B2 | 11/2003 | Francis |
| 6,653,525 B2 | 11/2003 | Ingenito |
| 6,659,106 B1 | 12/2003 | Hovda |
| 6,669,685 B1 | 12/2003 | Rizoiu |
| 6,669,694 B2 | 12/2003 | Shadduck |
| 6,673,071 B2 | 1/2004 | VanDusseldorp |
| 6,676,628 B2 | 1/2004 | Sussman |
| 6,676,629 B2 | 1/2004 | Andrew |
| 6,679,264 B1 | 1/2004 | Deem |
| 6,679,879 B2 | 1/2004 | Shadduck |
| 6,682,520 B2 | 1/2004 | Ingenito |
| 6,692,494 B1 | 2/2004 | Cooper |
| 6,695,839 B2 | 2/2004 | Sharkey |
| 6,699,244 B2 | 3/2004 | Carranza |
| 6,708,056 B2 | 3/2004 | Duchon |
| 6,712,811 B2 | 3/2004 | Underwood |
| 6,712,812 B2 | 3/2004 | Roschak |
| 6,716,252 B2 | 4/2004 | Lazarovitz |
| 6,719,738 B2 | 4/2004 | Mehier |
| 6,719,754 B2 | 4/2004 | Underwood |
| 6,719,755 B2 | 4/2004 | Sliwa, Jr. |
| 6,723,064 B2 | 4/2004 | Babaev |
| 6,726,684 B1 | 4/2004 | Woloszko |
| 6,726,696 B1 | 4/2004 | Houser |
| 6,726,708 B2 | 4/2004 | Lasheras |
| 6,730,079 B2 | 5/2004 | Lovewell |
| 6,734,405 B2 | 5/2004 | Centanni |
| 6,746,447 B2 | 6/2004 | Davison |
| 6,749,604 B1 | 6/2004 | Eggers |
| 6,755,794 B2 | 6/2004 | Soukup |
| 6,758,846 B2 | 7/2004 | Goble |
| 6,760,616 B2 | 7/2004 | Hoey |
| 6,763,836 B2 | 7/2004 | Tasto |
| 6,764,487 B2 | 7/2004 | Mulier |
| 6,766,202 B2 | 7/2004 | Underwood |
| 6,770,070 B1 | 8/2004 | Balbierz |
| 6,770,071 B2 | 8/2004 | Woloszko |
| 6,772,012 B2 | 8/2004 | Ricart |
| 6,773,431 B2 | 8/2004 | Eggers |
| 6,776,765 B2 | 8/2004 | Soukup |
| 6,776,780 B2 | 8/2004 | Mulier |
| 6,780,178 B2 | 8/2004 | Palanker |
| 6,780,180 B1 | 8/2004 | Goble |
| 6,805,130 B2 | 10/2004 | Tasto |
| 6,813,520 B2 | 11/2004 | Truckai |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | MacKool |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,911,028 B2 | 6/2005 | Shadduck |
| 6,915,806 B2 | 7/2005 | Pacek |
| 6,918,903 B2 | 7/2005 | Bass |
| 6,921,385 B2 | 7/2005 | Clements |
| 6,929,640 B1 | 8/2005 | Underwood |
| 6,929,642 B2 | 8/2005 | Xiao |
| 6,949,096 B2 | 9/2005 | Davison |
| 6,955,674 B2 | 10/2005 | Eick |
| 6,955,675 B2 | 10/2005 | Jain |
| 6,960,182 B2 | 11/2005 | Moutafis |
| 6,960,203 B2 | 11/2005 | Xiao |
| 6,960,204 B2 | 11/2005 | Eggers |
| 6,969,376 B2 | 11/2005 | Takagi |
| 6,972,014 B2 | 12/2005 | Eum |
| 6,986,769 B2 | 1/2006 | Nelson |
| 6,991,028 B2 | 1/2006 | Comeaux |
| 6,991,631 B2 | 1/2006 | Woloszko |
| 7,004,940 B2 | 2/2006 | Ryan |
| 7,004,941 B2 | 2/2006 | Tvinnereim |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,083,612 B2 | 8/2006 | Littrup |
| 7,087,040 B2 | 8/2006 | McGuckin, Jr. |
| 7,089,064 B2 | 8/2006 | Manker |
| 7,094,215 B2 | 8/2006 | Davison |
| 7,101,367 B2 | 9/2006 | Xiao |
| 7,104,986 B2 | 9/2006 | Hovda |
| 7,105,007 B2 | 9/2006 | Hibler |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Oray |
| 7,153,301 B2 | 12/2006 | Swartz |
| 7,169,143 B2 | 1/2007 | Eggers |
| 7,179,255 B2 | 2/2007 | Lettice |
| 7,186,234 B2 | 3/2007 | Dahla |
| 7,192,400 B2 | 3/2007 | Campbell |

(56) References Cited

U.S. PATENT DOCUMENTS

| | | |
|---|---|---|
| 7,192,428 B2 | 3/2007 | Eggers |
| 7,201,750 B1 | 4/2007 | Eggers |
| 7,217,268 B2 | 5/2007 | Eggers |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,297,143 B2 | 11/2007 | Woloszko |
| 7,297,145 B2 | 11/2007 | Woloszko |
| 7,320,325 B2 | 1/2008 | Duchon |
| 7,335,195 B2 | 2/2008 | Mehier |
| 7,335,197 B2 | 2/2008 | Sage |
| 7,340,307 B2 | 3/2008 | Maguire |
| 7,347,859 B2 | 3/2008 | Garabedian |
| 7,410,486 B2 | 8/2008 | Fuimaono |
| 7,419,500 B2 | 9/2008 | Marko |
| 7,429,262 B2 | 9/2008 | Woloszko |
| 7,435,250 B2 | 10/2008 | Francischelli |
| 7,470,228 B2 | 12/2008 | Connors |
| 7,503,904 B2 | 3/2009 | Choi |
| 7,512,445 B2 | 3/2009 | Truckai |
| 7,549,987 B2 | 6/2009 | Shadduck |
| 7,559,367 B2 | 7/2009 | Vinegar |
| 7,585,295 B2 | 9/2009 | Ben-Nun |
| 7,597,147 B2 | 10/2009 | Vitek |
| 7,674,259 B2 | 3/2010 | Shadduck |
| 7,678,111 B2 | 3/2010 | Mulier |
| 7,753,871 B2 | 7/2010 | Mehier |
| 7,831,133 B2 | 11/2010 | Vinegar |
| 7,892,229 B2 | 2/2011 | Shadduck |
| 7,993,323 B2 | 8/2011 | Barry |
| 8,014,711 B2 | 9/2011 | Ito |
| 8,016,823 B2 | 9/2011 | Shadduck |
| 8,145,113 B2 | 3/2012 | Murakami |
| 8,187,269 B2 | 5/2012 | Shadduck |
| 8,224,165 B2 | 7/2012 | Vinegar |
| 8,355,623 B2 | 1/2013 | Vinegar |
| 8,444,636 B2 | 5/2013 | Shadduck |
| 8,521,074 B2 | 8/2013 | Murakami |
| 8,579,892 B2 | 11/2013 | Hoey |
| 8,579,893 B2 | 11/2013 | Hoey |
| 8,585,645 B2 | 11/2013 | Barry |
| 8,721,632 B2 | 5/2014 | Hoey |
| 8,758,341 B2 | 6/2014 | Shadduck |
| 8,761,626 B2 | 6/2014 | Seo |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1* | 6/2002 | Shadduck ............... A61B 18/04 607/96 |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0161326 A1 | 10/2002 | Sussman |
| 2002/0177846 A1* | 11/2002 | Mulier et al. ................. 606/27 |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1* | 5/2003 | Swartz et al. ................. 606/41 |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0095168 A1 | 5/2005 | Centanni |
| 2005/0119650 A1 | 6/2005 | Sanders |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1* | 12/2005 | Truckai et al. .................. 606/41 |
| 2005/0283143 A1 | 12/2005 | Rizoiu |
| 2006/0004400 A1 | 1/2006 | McGurk |
| 2006/0036237 A1 | 2/2006 | Davison |
| 2006/0047291 A1 | 3/2006 | Barry |
| 2006/0085054 A1 | 4/2006 | Zikorus |
| 2006/0095032 A1* | 5/2006 | Jackson ............... A61B 5/1076 606/41 |
| 2006/0100619 A1 | 5/2006 | McClurken |
| 2006/0130830 A1 | 6/2006 | Barry |
| 2006/0135955 A1 | 6/2006 | Shadduck |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0276871 A1 | 12/2006 | Lamson |
| 2007/0032785 A1 | 2/2007 | Diederich |
| 2007/0036417 A1 | 2/2007 | Argiro |
| 2007/0091087 A1 | 4/2007 | Zuiderveld |
| 2007/0142846 A1 | 6/2007 | Catanese |
| 2007/0225744 A1 | 9/2007 | Nobles |
| 2007/0225750 A1 | 9/2007 | Ren |
| 2007/0239197 A1 | 10/2007 | Dubey |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | McLean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |

(56) References Cited

U.S. PATENT DOCUMENTS

| | | |
|---|---|---|
| 2008/0039876 A1 | 2/2008 | Catanese |
| 2008/0039893 A1 | 2/2008 | McLean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0208187 A1 | 8/2008 | Bhushan |
| 2008/0249399 A1 | 10/2008 | Appling |
| 2008/0275440 A1 | 11/2008 | Kratoska |
| 2008/0281267 A1 | 11/2008 | Mehier |
| 2009/0018553 A1 | 1/2009 | McLean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1 | 8/2009 | Hoey |
| 2009/0227998 A1 | 9/2009 | Aljuri |
| 2009/0277457 A1 | 11/2009 | Hoey |
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1* | 3/2010 | Hoey et al. .................. 606/2 |
| 2010/0094270 A1 | 4/2010 | Sharma |
| 2010/0114083 A1 | 5/2010 | Sharma |
| 2010/0145254 A1 | 6/2010 | Shadduck |
| 2010/0145325 A1 | 6/2010 | Hoey |
| 2010/0145326 A1 | 6/2010 | Hoey |
| 2010/0160905 A1 | 6/2010 | Shadduck |
| 2010/0179416 A1 | 7/2010 | Hoey |
| 2010/0179528 A1 | 7/2010 | Shadduck |
| 2010/0262133 A1 | 10/2010 | Hoey |
| 2010/0286679 A1 | 11/2010 | Hoey |
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0238144 A1 | 9/2011 | Hoey |
| 2011/0264090 A1 | 10/2011 | Shadduck |
| 2012/0065632 A1 | 3/2012 | Shadduck |
| 2012/0116376 A1 | 5/2012 | Hoey |
| 2012/0259271 A1 | 10/2012 | Shadduck |
| 2013/0006231 A1 | 1/2013 | Sharma |

FOREIGN PATENT DOCUMENTS

| | | |
|---|---|---|
| WO | 9953853 | 10/1999 |
| WO | 0029055 | 5/2000 |
| WO | 0124715 | 4/2001 |
| WO | 02069821 | 9/2002 |
| WO | 03070302 | 8/2003 |
| WO | 03086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006055695 | 5/2006 |
| WO | 2006108974 | 10/2006 |
| WO | 2009009398 | 1/2009 |
| WO | 2010042461 | 4/2010 |
| WO | 2012167213 | 12/2012 |
| WO | 2014113724 | 7/2014 |

OTHER PUBLICATIONS

International Search Report for PCT/US2009/059609, Mar. 5, 2010.
International Search Report for PCT/US2012/040639, Dec. 18, 2012.
Hai; Photoselective Vaporization Prostatectomy: A Palliative Treatment Option for Men with Urinary Obstruction Secondary to Prostate Cancer; PCRI Prost. Cancer Rsrch. Inst. Reprint. from PCRI Insights Nov. 2005, vol. 8(4); pp. 4.
Van De Velde; Vapo-cauterization of the uterus; Amer. J. Med. Sci.; vol. CXVII; 1899.
Blacker; Vaporization of the uterus; J. Obstet. & Gyn.; pp. 488-511; 1901.
Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.
Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi:10.1136/gut.2005.086777.
Sharma et al; Balloon-based, cicrumferential, endoscopic radiofrequency ablation of Barrett's esophagus: 1-year follow-up of 100 patients (with video); Gastrointestinal Endoscopy; 2007; vol. 65, No. 2; 0016-5/$32.00 doi:10.1016/j.gie.2006.09.033; pp. 185-195.
Sanfilippo et al; Update: Options in Endometrial Ablation; Supplement to OBG Management; Dec. 2009; pp. S1-S24; Dowden Health Media.
United States FDA; Summary of Safety and Effectiveness Data: Cryogen, Inc.: Her Option Uterine Cryoablation Therapy System; PMA P000032; Sep. 14, 2001; pp. 1-22.
American Medical Systems, Inc.; her option office cryoablation therapy Resource Guide; 2007; pp. 1-29; American Medical Systems, Inc.. 10700 Bren Road West, Minnetonka, MN 55343 USA.
Boston Scientific; HTA System Endometrial Ablation System; 2006; BVU 1090 Rev. A 10M 9/06-9/08; Boston Scientific Corporation, One Boston Scientific Place, Natick, MA 01760-1537.
Ethicon Women's Health & Urology; Instructions for Use, Gynecare Thermachoice III Uterine Balloon Therapy System, Thermal Balloon Ablation Silicone Catheter and Syrings (Single-Use); Mar. 26, 2008; pp. 1-156; TCIII_389630.R06_Main.indd; Gynecare, a divsion of Ethicon, Inc. a Johnson & Johnson company, Sommerville, NJ, 08876-0151 USA.
Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.
Carter; Endometrial Ablation: More Choices, More Options; The Female Patient; 2005; pp. 35-40; 30(12).
Thibeau; AW-06995-001 ; Text, Manual, Novasure, V1, EN, US; Aug. 26, 2011; pp. 1-23; Hologic, Inc.
Neuwirth et al.; The endometrial ablator: a new instrument; Obst. & Gyn.; vol. 83; No. 5; part 1; pp. 792-796; 1994.
Prior et al.; Treatment of mennorrhagia by radiofrequency heating; Int. J. Hyperthermia; vol. 7; No. 2; pp. 213-220; 1991.
International Search Report for PCT/US2014/012131, Jul. 30, 2014.

* cited by examiner

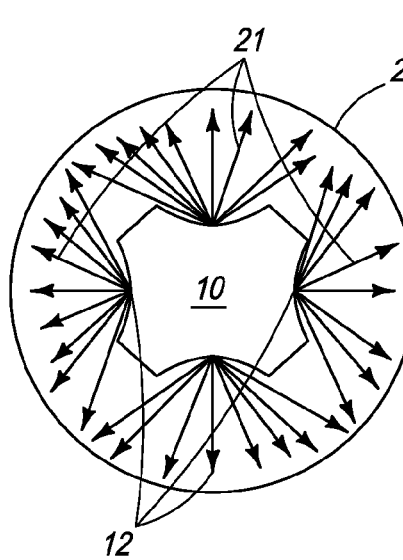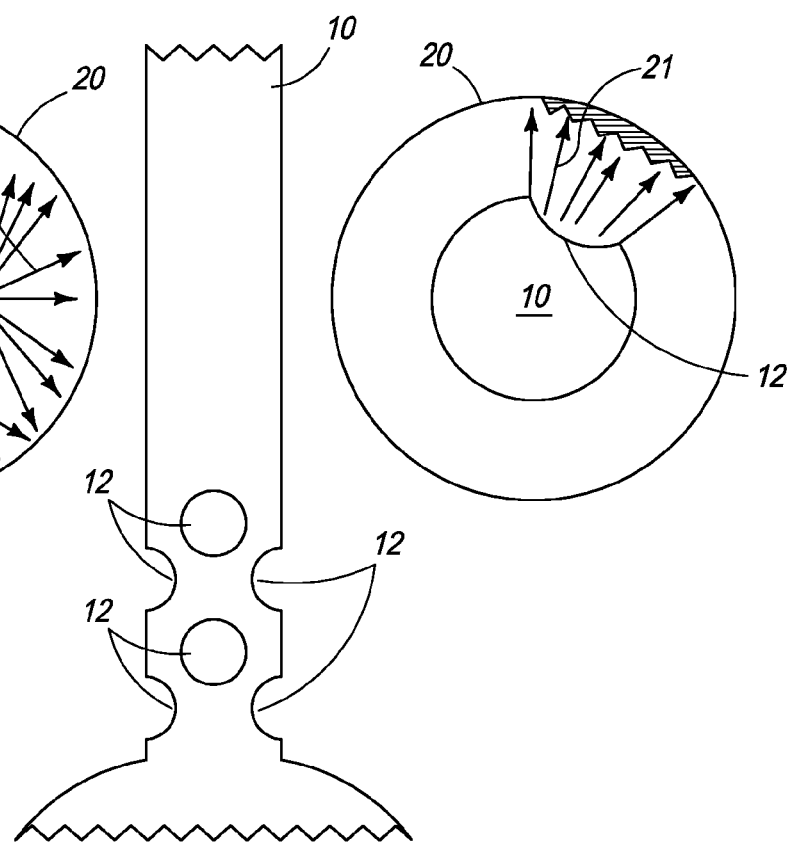
FIG. 2B
FIG. 2C
FIG. 2A

METHOD AND APPARATUS FOR THE ABLATION OF GASTROINTESTINAL TISSUE

CROSS-REFERENCE

The present invention relies on U.S. Provisional Application No. 61/102,885, filed on Oct. 6, 2008, for priority and is hereby incorporated herein by reference.

FIELD OF THE INVENTION

The present invention relates to medical apparatus and procedures. More particularly, the present invention relates to a device for ablation of tissue in a hollow organ comprising a centering or positioning attachment in order to position the device at a consistent distance from the tissue to be ablated.

BACKGROUND OF THE INVENTION

Colon polyps affect almost 25% of the population over the age of 50. While most polyps are detected on colonoscopy and easily removed using a snare, flat sessile polyps are hard to remove using the snare technique and carry a high risk of complications, such as bleeding and perforation. Recently, with improvement in imaging techniques, more flat polyps are being detected. Endoscopically unresectable polyps require surgical removal. Most colon cancer arises from colon polyps and, safe and complete resection of these polyps is imperative for the prevention of colon cancer.

Barrett esophagus is a precancerous condition effecting 10-14% of US population with gastro esophageal reflux disease (GERD) and is the proven precursor lesion of esophageal adenocarcinoma, the fastest rising cancer in the developed nations. The incidence of the cancer has risen over 6 fold in the last 2 decades and mortality has risen by 7 fold. The 5-year mortality from esophageal cancer is 85%. Ablation of Barrett epithelium has shown to prevent its progression to esophageal cancer.

Dysfunctional uterine bleeding (DUB), or menorrhagia, affects 30% of women in reproductive age. These symptoms have considerable impact on a woman's health and quality of life. The condition is typically treated with endometrial ablation or a hysterectomy. The rates of surgical intervention in these women are high. Almost 30% of women in US will undergo hysterectomy by the age 60, with menorrhagia or DUB being the cause for surgery in 50-70% of these women. Endometrial ablation techniques have been FDA approved for women with abnormal uterine bleeding and with intra-mural fibroids less than 2 cm. The presence of submucosal uterine fibroids and a large uterus size have been shown to decrease the efficacy of standard endometrial ablation. Of the five FDA approved global ablation devices (namely, Thermachoice, hydrothermal ablation, Novasure, Her Option, and microwave ablation) only microwave ablation (MEA) has been approved for use where the submucosal fibroids are less than 3 cm and are not occluding the endometrial cavity and, additionally, for large uteri up to 14 cm.

The known ablation treatments for Barrett esophagus include laser treatment (Ertan et al, Am. J. Gastro., 90:2201-2203 [1995]), ultrasonic ablation (Bremner et al, Gastro. Endo., 43:6 [1996]), photodynamic therapy (PDT) using photo-sensitizer drugs (Overholt et al, Semin. Surq. Oncol., 1:372-376 (1995), multipolar electrocoagulation such as by use of a bicap probe (Sampliner et al,), Argon Plasma Coagulation (APC;), Radiofrequency ablation (Sharma et al. Gastrointest Endosc) and cryoablation (Johnston et al. Gastrointest Endosc). The treatments are delivered with the aid of an endoscope and devices passed through the channel of endoscope or alongside the endoscope.

Conventional techniques have inherent limitations, however, and have not found widespread clinical applications. First, most of the hand held ablation devices (Bicap probe, APC, cryoablation) are point and shoot devices that create small foci of ablation. This ablation mechanism is operator dependent, cumbersome and time consuming. Second, because the target tissue is moving due to patient movement, respiration movement, normal peristalsis and vascular pulsations, the depth of ablation of the target tissue is inconsistent and results in a non-uniform ablation. Superficial ablation results in incomplete ablation with residual neoplastic tissue left behind. Deeper ablation results in complications such as bleeding, stricture formation and perforation. All of these limitations and complications have been reported with conventional devices.

For example, radiofrequency ablation uses a rigid bipolar balloon based electrode and radiofrequency thermal energy. The thermal energy is delivered by direct contact of the electrode with the diseased Barrett epithelium allowing for a relatively uniform, large area ablation. However, the rigid electrode does not accommodate for variations in esophageal size and is ineffective in ablating tortuous esophagus, proximal esophageal lesions as an esophagus narrows towards the top, and esophagus at the gastroesophagal junction due to changes in the esophagus diameter. Nodular disease in Barrett esophagus also cannot be treated using the rigid bipolar RF electrode. Due to its size and rigidity, the electrode cannot be passed through the scope. In addition sticking of sloughed tissue to the electrode impedes with delivery of radiofrequency energy resulting in incomplete ablation. The electrode size is limited to 3 cm, thus requiring repeat applications to treat larger lengths of Barrett esophagus.

Photodynamic therapy (PDT) is a two part procedure that involves injecting a photo-sensitizer that is absorbed and retained by the neoplastic and pre-neoplastic tissue. The tissue is then exposed to a selected wavelength of light which activates the photo-sensitizer and results in tissue destruction. PDT is associated with complications such as stricture formation and photo-sensitivity which has limited its use to the most-advanced stages of the disease. In addition, patchy uptake of the photosensitizer results in incomplete ablation and residual neoplastic tissue.

Cryoablation of the esophageal tissues via direct contact with a liquid nitrogen has been studied in both animal models and humans (Rodgers et al, Cryobiology, 22:86-92 (1985); Rodgers et al, Ann. Thorac. Surq. 55:52-7 [1983]) and has been used to treat Barrett esophagus and (Johnston et al. Gastrointest Endosc) early esophageal cancer (Grana et al, Int. Surg., 66:295 [1981]). A spray catheter that directly sprays liquid $N_2$ or $CO_2$ (cryoablation) or argon (APC) to ablate Barrett tissue in the esophagus has been described. These techniques suffer the shortcoming of the traditional hand-held devices. Treatment using this probe is cumbersome and requires operator control under direct endoscopic visualization. Continuous movement in the esophagus due to respiration or cardiac or aortic pulsations or movement causes an uneven distribution of the ablative agent and results in non-uniform and/or incomplete ablation. Close or direct contact of the catheter to the surface epithelium may cause deeper tissue injury, resulting in perforation, bleeding or stricture formation. Too distant a placement of the catheter due to esophageal movement will result in incomplete Barrett ablation, requiring multiple treatment sessions or buried lesions with a continued risk of esophageal cancer. Expansion of cryogenic gas in the esophagus results in uncontrolled retching which may result in esophageal tear or perforation requiring continued suctioning of cryogen.

Colon polyps are usually resected using snare resection with or without the use of monopolar cautery. Flat polyps or residual polyps after snare resection have been treated with argon plasma coagulation or laser treatment. Both these treatments, have the previously mentioned limitations. Hence, most large flat polyps undergo surgical resection due to high risk of bleeding, perforation and residual disease using traditional endoscopic resection or ablation techniques.

Most of the conventional balloon catheters traditionally used for tissue ablation either heat or cool the balloon itself or a heating element such as a radio frequency (RF) coils mounted on the balloon. This requires direct contact of the balloon catheter with the ablated surface. When the balloon catheter is deflated, the epithelium sticks to the catheter and sloughs off, thereby causing bleeding. Blood can interfere with delivery of energy i.e. energy sink. In addition reapplication of energy will result in deeper burn in the area where superficial lining has sloughed. Further, balloon catheters cannot be employed for treatment in non cylindrical organs, like the uterus or sinuses, and also do not provide non-circumferential or focal ablation in a hollow organ. Additionally, if used with cryogens as ablative agents, which expand exponentially upon being heated, balloon catheters may result in a closed cavity and trap the escape of cryogen, resulting in complications such as perforations and tears.

Accordingly, there is a need in the art for an improved method and system for delivering ablative agents to a tissue surface, for providing a consistent, controlled, and uniform ablation of the target tissue, and for minimizing the adverse side effects of introducing ablative agents into a patient.

SUMMARY OF THE INVENTION

The present invention is directed toward a device to perform ablation of endometrial tissue, comprising a catheter having a shaft through which an ablative agent can travel, a first positioning element attached to said catheter shaft at a first position, wherein said first positioning element is configured to center said catheter in a center of a cervix, and a second positioning element attached to said catheter shaft at a second position, wherein the shaft comprises a plurality of ports through which said ablative agent can be released out of said shaft and wherein said ports are located between said first position and second position.

Optionally, the first positioning element is conical. The first positioning element comprises an insulated membrane which can be configured to prevent an escape of thermal energy through the cervix. The second positioning element is disc shaped. The second positioning element has a dimension which can be used to determine a uterine cavity size. The second positioning element has a dimension which can be used to calculate an amount of thermal energy needed to ablate the endometrial tissue. The device also includes at least one temperature sensor, which can be used to control delivery of the ablative agent, such as steam.

Optionally, the second positioning element is separated from endometrial tissue to be ablated by a distance of greater than 0.1 mm. The first positioning element is a covered wire mesh. The first positioning element is comprises a circular body with a diameter between 0.1 mm and 10 cm. The second positioning element is oval and wherein said oval has a long axis between 0.1 mm and 10 cm and a short axis between 0.1 mm and 5 cm.

In another embodiment, the present invention is directed toward a device to perform ablation of endometrial tissue, comprising a catheter having a hollow shaft through which steam can be delivered, a first positioning element attached to said catheter shaft at a first position, wherein said first positioning element is conical and configured to center said catheter in a center of a cervix, a second positioning element attached to said catheter shaft at a second position, wherein the second positioning element is disc shaped, a plurality of ports integrally formed in said catheter shaft, wherein steam can be released out of said ports and directed toward endometrial tissue and wherein said ports are located between said first position and second position; and at least one temperature sensor.

Optionally, the second positioning element has a dimension, which can be used to determine a uterine cavity size. The second positioning element has a dimension, which can be used to calculate an amount of thermal energy needed to ablate the endometrial tissue. The temperature sensors are used to control delivery of said ablative agent. The first positioning element comprises wire mesh. The second positioning element has a disc shape that is oval and wherein said oval has a long axis between 0.1 mm and 10 cm and a short axis between 0.1 mm and 5 cm.

A device to perform ablation of tissue in a hollow organ, comprising a catheter having a shaft through which an ablative agent can travel; a first positioning element attached to said catheter shaft at a first position, wherein said first positioning element is configured to position said catheter at a predefined distance from the tissue to be ablated; and wherein the shaft comprises one or more port through which said ablative agent can be released out of said shaft.

Optionally, the device further comprises a second positioning element attached to said catheter shaft at a position different from said first positioning element. The first positioning element is at least one of a conical shape, disc shape, or a free form shape conformed to the shape of the hollow organ. The second positioning element has predefined dimensions and wherein said predefined dimensions are used to determine the dimensions of the hollow organ to be ablated. The first positioning element comprises an insulated membrane. The insulated membrane is configured to prevent an escape of thermal energy. The second positioning element is at least one of a conical shape, disc shape, or a free form shape conformed to the shape of the hollow organ. The second positioning element has predefined dimensions and wherein said predefined dimensions are used to determine the dimensions of the hollow organ to be ablated. The second positioning element has a predefined dimension and wherein said predefined dimension is used to calculate an amount of thermal energy needed to ablate the tissue. The device further comprises at least one temperature sensor. The temperature sensor is used to control delivery of said ablative agent. The ablative agent is steam. The first positioning element is a covered wire mesh. The first positioning element comprises a circular body with a diameter between 0.01 mm and 10 cm. The first positioning element is oval and wherein said oval has a long axis between 0.01 mm and 10 cm and a short axis between 0.01 mm and 9 cm.

In another embodiment, the present invention is directed to a device to perform ablation of tissue in a hollow organ, comprising a catheter having a hollow shaft through which steam can be delivered; a first positioning element attached to said catheter shaft at a first position, wherein said first positioning element is configured to position said catheter at a predefined distance from the surface of the hollow organ; a second positioning element attached to said catheter shaft at a second position, wherein the second positioning element is shaped to position said catheter at a predefined distance from the surface of the hollow organ; a plurality of ports integrally formed in said catheter shaft, wherein steam can be released out of said ports and directed toward tissue to be ablated and wherein said ports are located between said first position and second position; and at least one temperature sensor.

Optionally, the first positioning element has a predefined dimension and wherein said dimension is used to determine the size of the hollow organ. The second positioning element has a predefined dimension and wherein said dimension is used to calculate an amount of thermal energy needed to ablate the tissue. The temperature sensor is used to control delivery of said ablative agent. The first positioning element comprises wire mesh. The second positioning element has a disc shape that is oval and wherein said oval has a long axis between 0.01 mm and 10 cm and a short axis between 0.01 mm and 9 cm.

In another embodiment, the present invention is directed to a device to perform ablation of the gastrointestinal tissue, comprising a catheter having a shaft through which an ablative agent can travel; a first positioning element attached to said catheter shaft at a first position, wherein said first positioning element is configured to position the catheter at a fixed distance from the gastrointestinal tissue to be ablated, and wherein said first positioning element is separated from an ablation region by a distance of between 0 mm and 5 cm, and an input port at a second position and in fluid communication with said catheter shaft in order to receive said ablative agent wherein the shaft comprises one or more ports through which said ablative agent can be released out of said shaft.

Optionally, the first positioning element is at least one of an inflatable balloon, wire mesh disc or cone. By introducing said ablative agent into said ablation region, the device creates an gastrointestinal pressure equal to or less than 5 atm. The ablative agent has a temperature between −100 degrees Celsius and 200 degrees Celsius. The catheter further comprises a temperature sensor. The catheter further comprises a pressure sensor. The first positioning element is configured to abut a gastroesophageal junction when placed in a gastric cardia. The ports are located between said first position and second position. The diameter of the positioning element is between 0.01 mm and 100 mm. The ablative agent is steam. The first positioning element comprises a circular body with a diameter between 0.01 mm and 10 cm.

In another embodiment, the present invention is directed toward a device to perform ablation of esophageal tissue, comprising a catheter having a hollow shaft through which steam can be transported; a first positioning element attached to said catheter shaft at a first position, wherein said first positioning element is configured to abut a gastroesophageal junction when placed in a gastric cardia; and an input port at a second position and in fluid communication with said catheter shaft in order to receive said steam wherein the shaft comprises a plurality of ports through which said steam can be released out of said shaft and wherein said ports are located between said first position and second position. The device further comprises a temperature sensor wherein said temperature sensor is used to control the release of said steam. The first positioning element comprises at least one of a wire mesh disc, a wire mesh cone, or an inflatable balloon. The first positioning element is separated from an ablation region by a distance of between 0 mm and 1 cm. The diameter of the first positioning element is between 1 mm and 100 mm.

In another embodiment, the present invention is directed to a device to perform ablation of gastrointestinal tissue, comprising a catheter having a hollow shaft through which steam can be transported; a first positioning element attached to said catheter shaft at a first position, wherein said first positioning element is configured to abut the gastrointestinal tissue; and an input port at a second position and in fluid communication with said catheter shaft in order to receive said steam wherein the shaft comprises one or more ports through which said steam can be released out of said shaft onto the gastrointestinal tissue.

Optionally, the device further comprises a temperature sensor wherein said temperature sensor is used to control the release of said steam. The first positioning element comprises at least one of a wire mesh disc and a wire mesh cone. The diameter of the first positioning element is 0.1 mm to 50 mm. The device is used to perform non-circumferential ablation.

In another embodiment, the present invention is directed to a device to perform ablation of endometrial tissue, comprising a catheter having a shaft through which an ablative agent can travel; a first positioning element attached to said catheter shaft at a first position, wherein said first positioning element is configured to center said catheter in a center of a cervix; and a shaft comprises a plurality of ports through which said ablative agent can be released out of said shaft.

Optionally, the device further comprises a second positioning element attached to said catheter shaft at a second position. The first positioning element is conical. The first positioning element comprises an insulated membrane. The insulated membrane is configured to prevent an escape of thermal energy through the cervix. The second positioning element is disc shaped. The second positioning element has a predefined dimension and wherein said dimension is used to determine a uterine cavity size. The second positioning element has a predefined dimension and wherein said dimension is used to calculate an amount of thermal energy needed to ablate the endometrial tissue. The device further comprises at least one temperature sensor wherein said temperature sensor is used to control delivery of said ablative agent. The ablative agent is steam. The first positioning element is a covered wire mesh. The first positioning element comprises a circular body with a diameter between 0.01 mm and 10 cm. The second positioning element is oval and wherein said oval has a long axis between 0.01 mm and 10 cm and a short axis between 0.01 mm and 5 cm.

In another embodiment, the present invention is directed toward a device to perform ablation of endometrial tissue, comprising a catheter having a hollow shaft through which steam can be delivered; a first positioning element attached to said catheter shaft at a first position, wherein said first positioning element is conical and configured to center said catheter in a center of a cervix; a second positioning element attached to said catheter shaft at a second position, wherein the second positioning element is elliptical shaped; a plurality of ports integrally formed in said catheter shaft, wherein steam can be released out of said ports and directed toward endometrial tissue and wherein said ports are located between said first position and second position; and at least one temperature sensor.

Optionally, the second positioning element has a predefined dimension and wherein said dimension is used to determine a uterine cavity size. The second positioning element has a diameter and wherein said diameter is used to calculate an amount of thermal energy needed to ablate the endometrial tissue. The temperature sensors are used to control delivery of said ablative agent. The first positioning element comprises wire mesh. The second positioning element has a disc shape that is oval and wherein said oval has a long axis between 0.01 mm and 10 cm and a short axis between 0.01 mm and 5 cm.

Optionally, the second positioning element can use one or more sources of infrared, electromagnetic, acoustic or radiofrequency energy to measure the dimensions of the hollow cavity. The energy is emitted from the sensor and is reflected back to the detector in the sensor. The reflected data is used to determine the dimension of the hollow cavity.

BRIEF DESCRIPTION OF THE DRAWINGS

The present invention is described by way of embodiments illustrated in the accompanying drawings wherein:

FIG. 2a illustrates a longitudinal section of an ablation device with ports distributed thereon;

FIG. 2b illustrates a cross section of a port on the ablation device, in accordance with an embodiment of the present invention;

FIG. 2c illustrates a cross section of a port on the ablation device, in accordance with another embodiment of the present invention;

DETAILED DESCRIPTION OF THE INVENTION

Figure 1:
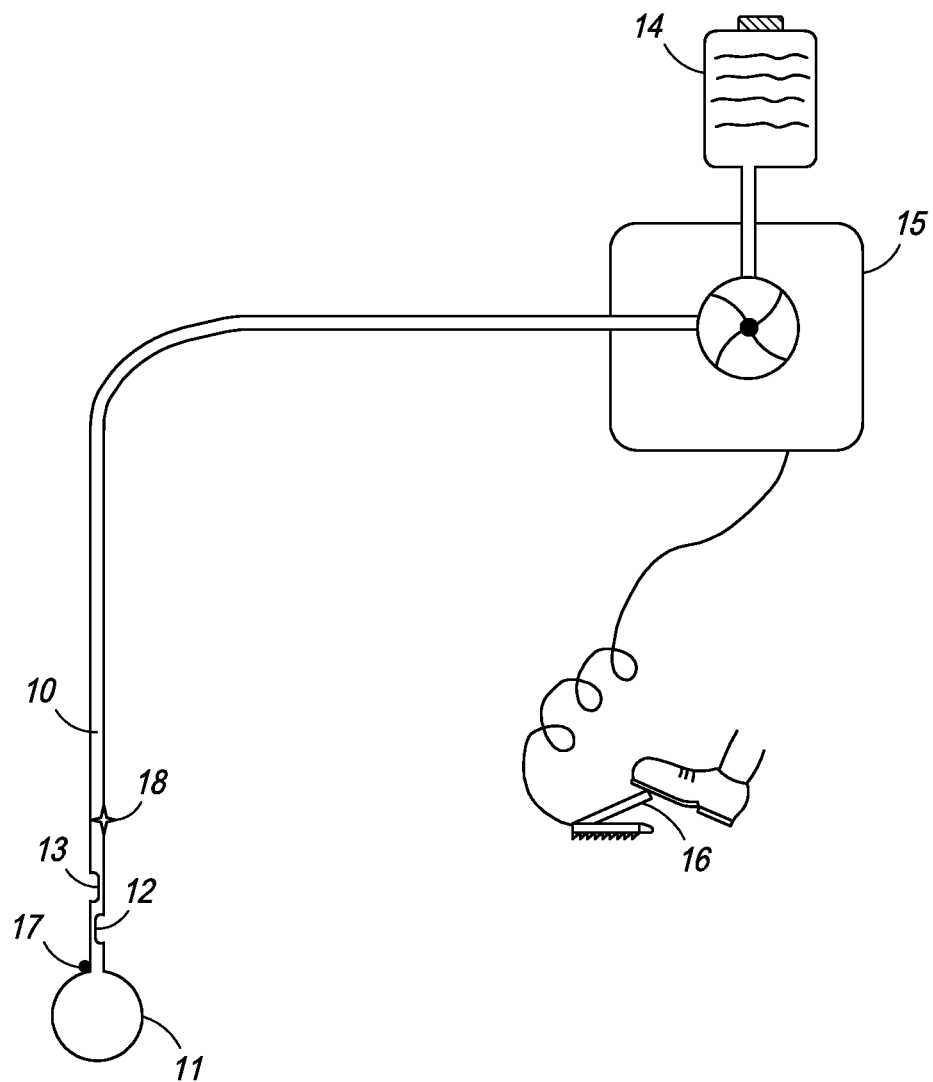
FIG. 1. illustrates an ablation device, in accordance with an embodiment of the present invention.

The present invention provides an ablation device comprising a catheter with one or more centering or positioning attachments at one or more ends of the catheter to affix the catheter and its infusion port at a fixed distance from the ablative tissue which is not affected by the movements of the organ. The arrangement of one or more spray ports allows for uniform spray of the ablative agent producing a uniform ablation of large area such as Barrett esophagus. The flow of ablative agent is controlled by the microprocessor and depends upon one or more of the length or area of tissue to be ablated, type and depth of tissue to be ablated and distance of the infusion port from the tissue to be ablated.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Ablative agents such as steam, heated gas or cryogens such as but not limited to liquid nitrogen are inexpensive and readily available, and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. The present invention will now be discussed in context of embodiments as illustrated by the accompanying drawings.

FIG. 1 illustrates an ablation device, in accordance with an embodiment of the present invention. The ablation device comprises a catheter 10 having a distal centering or positioning attachment which is an inflatable balloon 11. The catheter 10 is made of or covered with an insulated material to prevent the escape of ablative energy from the catheter body. The ablation device comprises one or more infusion ports 12 for the infusion of ablative agent and one or more suction ports 13 for the removal of ablative agent. In one embodiment, the infusion port 12 and suction port 13 are the same. Ablative agent is stored in a reservoir 14 connected to the catheter 10. Delivery of the ablative agent is controlled by a microprocessor 15 and initiation of the treatment is controlled by a treating physician using an input device, such as a foot-paddle 16. In other embodiments, the input device could be a voice recognition system (that is responsive to commands such as "start", "more", "less", etc.), a mouse, a switch, footpad, or any other input device known to persons of ordinary skill in the art. In one embodiment, microprocessor 15 translates signals from the input device, such as pressure being placed on the foot-paddle or vocal commands to provide "more" or "less" ablative agent, into control signals that determine whether more or less ablative agent is dispensed. Optional sensor 17 monitors changes in an ablative tissue or its vicinity to guide flow of ablative agent. Optional infrared, electromagnetic, acoustic or radiofrequency energy emitter and sensor 18 measures the dimensions of the hollow organ.

In one embodiment, the inflatable balloon has a diameter of between 1 mm and 10 cm. In one embodiment, the inflatable balloon is separated from the ports by a distance of 1 mm to 10 cm. In one embodiment, the size of the port openings are between 1 μm and 1 cm. It should be appreciated that the inflatable balloon is used to fix the device and therefore is configured to not contact the ablated area. The inflatable balloon can be any shape that contacts the hollow organ at 3 or more points. One of ordinary skill in the art that, using triangulation, one can calculate the distance of the catheter from the lesion. Alternatively the infrared, electromagnetic, acoustic or radiofrequency energy emitter and sensor 18 can measure the dimensions of the hollow organ. The infrared, electromagnetic, acoustic or radiofrequency energy is emitted from the emitter 18 and is reflected back from the tissue to the detector in the emitter 18. The reflected data can be used to determine the dimension of the hollow cavity. It should be appreciated that the emitter and sensor 18 can be incorporated into a single transceiver that is capable of both emitting energy and detecting the reflected energy.

FIG. 2a illustrates a longitudinal section of the ablation device, depicting a distribution of infusion ports. FIG. 2b illustrates a cross section of a distribution of infusion ports on the ablation device, in accordance with an embodiment of the present invention. The longitudinal and cross sectional view of the catheter 10 as illustrated in FIGS. 2a and 2b respectively, show one arrangement of the infusion ports 12 to produce a uniform distribution of ablative agent 21 in order to provide a circumferential area of ablation in a hollow organ 20. FIG. 2c illustrates a cross section of a distribution of infusion ports on the ablation device, in accordance with another embodiment of the present invention. The arrangement of the infusion ports 12 as illustrated in FIG. 2c produce a focal distribution of ablative agent 21 and a focal area of ablation in a hollow organ 20.

For all embodiments described herein, it should be appreciated that the size of the port, number of ports, and distance between the ports will be determined by the volume of ablative agent needed, pressure that the hollow organ can withstand, size of the hollow organ as measured by the distance of the surface from the port, length of the tissue to be ablated (which is roughly the surface area to be ablated), characteristics of the tissue to be ablated and depth of ablation needed. In one embodiment, there is at least one port opening that has a diameter between 1 μm and 1 cm. In another embodiment, there is two or more port openings that have a diameter between 1 μm and 1 cm and that are equally spaced around the perimeter of the device.

Figure 2D:
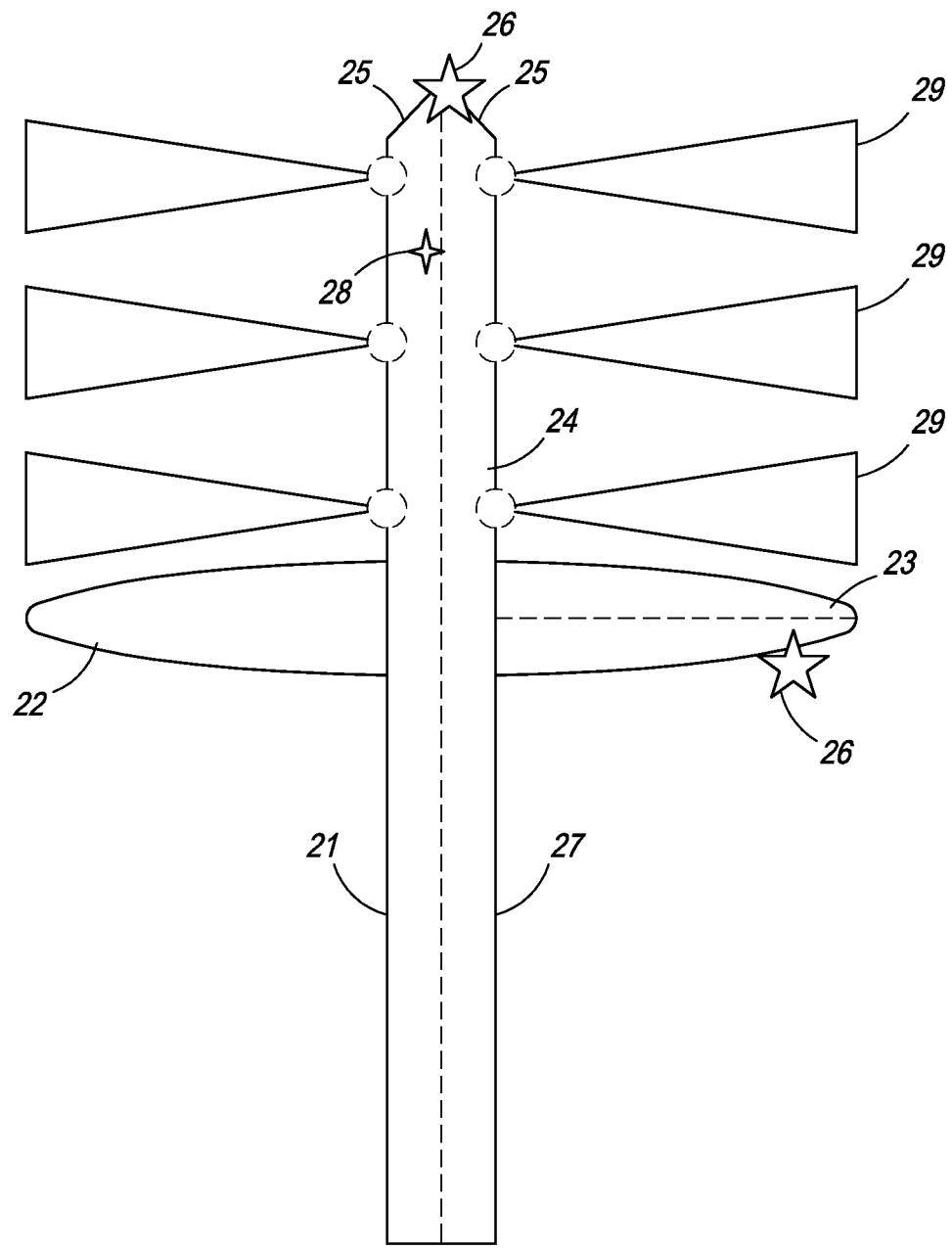
FIG. 2d illustrates a catheter of the ablation device, in accordance with an embodiment of the present invention.

FIG. 2d illustrates another embodiment of the ablation device. The vapor ablation catheter comprises an insulated catheter 21 with one or more positioning attachments 22 of known length 23. The vapor ablation catheter has one or more vapor infusion ports 25. The length 24 of the vapor ablation catheter 21 with infusion ports 25 is determined by the length or area of the tissue to be ablated. Vapor 29 is delivered through the vapor infusion ports 25. The catheter 21 is preferably positioned in the center of the positioning attachment 22, and the infusion ports 25 are arranged circumferentially for circumferential ablation and delivery of vapor. In another embodiment, the catheter 21 can be positioned toward the periphery of the positioning attachment 22 and the infusion ports 25 can be arranged non-circumferentially, preferably linearly on one side for focal ablation and delivery of vapor. The positioning attachment 23 is one of an inflatable balloon, a wire mesh disc with or without an insulated membrane covering the disc, a cone shaped attachment, a ring shaped attachment or a freeform attachment designed to fit the desired hollow body organ or hollow body passage, as further described below. Optional infrared, electromagnetic, acoustic or radiofrequency energy emitter and sensor 28 are incorporated to measures the dimensions of the hollow organ.

The vapor ablation catheter may also comprise an optional coaxial sheet 27 to restrain the positioning attachment 22 in a manner comparable to a coronary metal stent. In one embodiment, the disc is made of memory metal or memory material with a compressed linear form and a non-compressed form in the shape of the positioning attachment. Alternatively, the channel of an endoscope may perform the function of restraining the positioning attachment 22 by, for example, acting as a constraining sheath. Optional sensor 26 is deployed on the catheter to measure changes associated with vapor delivery or ablation. The sensor is one of temperature, pressure, photo or chemical sensor.

Optional, one or more, infrared, electromagnetic, acoustic or radiofrequency energy emitter and sensor 28 can measure the dimensions of the hollow organ. The infrared, electromagnetic, acoustic or radiofrequency energy is emitted from the emitter 18 and is reflected back from the tissue to the detector in the emitter 18. The reflected data can be used to determine the dimension of the hollow cavity. The measurement is performed at one or multiple points to get an accurate estimate of the dimension of the hollow organ. The data can also be used to create a topographic representation of the hollow organ.

Figure 3A:
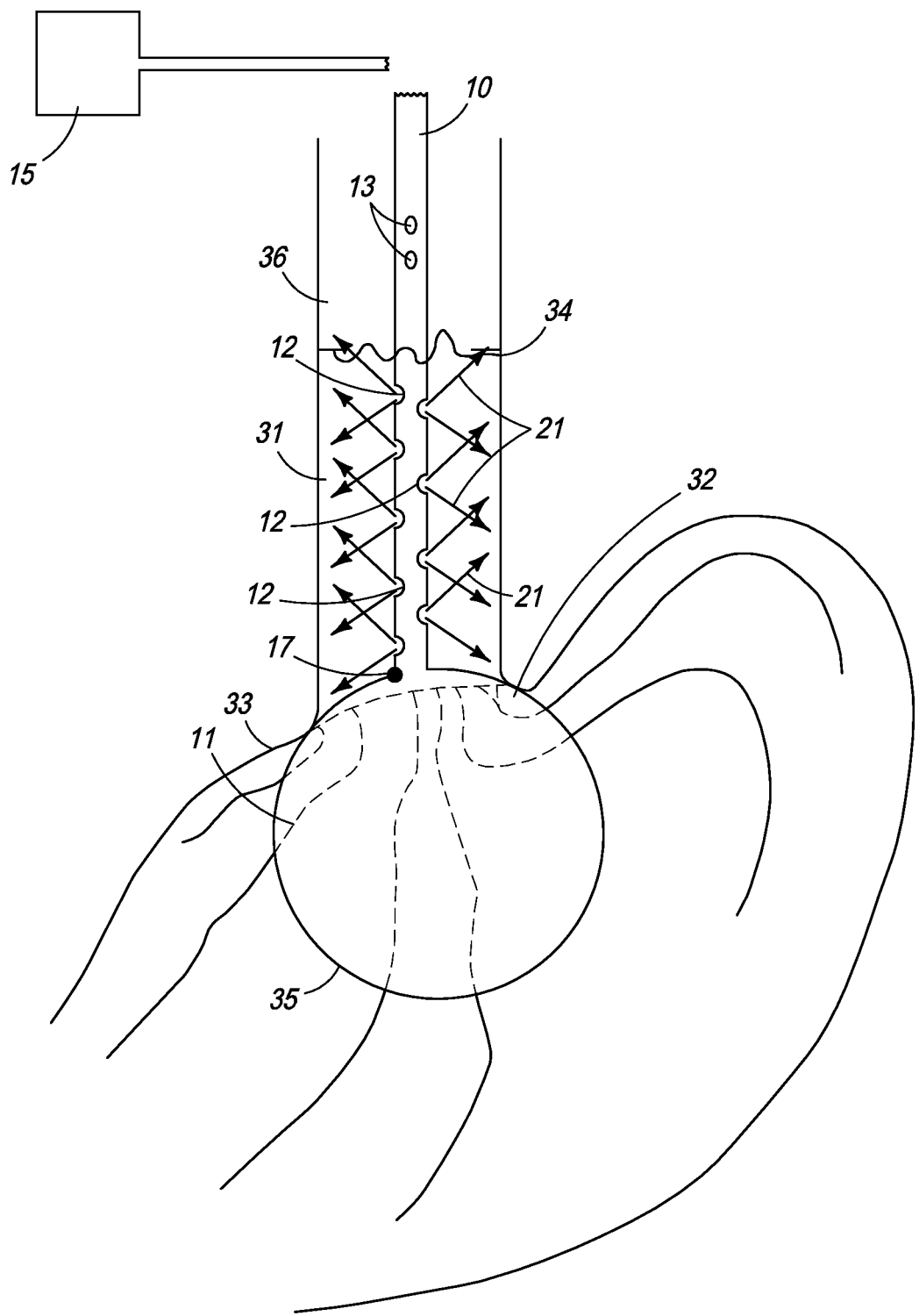
FIG. 3a. illustrates the ablation device placed in an upper gastrointestinal tract with Barrett esophagus to selectively ablate the Barrett tissue, in accordance with an embodiment of the present invention.

FIG. 3a illustrates the ablation device placed in an upper gastrointestinal tract with Barrett esophagus to selectively ablate the Barrett tissue, in accordance with an embodiment of the present invention. The upper gastrointestinal tract comprises Barrett esophagus 31, gastric cardia 32, gastroesophageal junction 33 and displaced squamo-columnar junction 34. The area between gastroesophageal junction 33 and displaced squamo-columnar junction 34 is Barrett esophagus 31, which is targeted for ablation. Distal to the cardia 32 is the stomach 35 and proximal to the cardia 32 is the esophagus 36. The ablation device is passed into the esophagus 36 and the positioning device 11 is placed in the gastric cardia 32 abutting the gastroesophageal junction 33. This affixes the ablation catheter 10 and its ports 12 in the center of the esophagus 36 and allows for uniform delivery of the ablative agent 21 to the Barrett esophagus 31. In one embodiment, the positioning device is first affixed to an anatomical structure, not being subjected to ablation, before ablation occurs. Where the patient is undergoing circumferential ablation or first time ablation, the positioning attachment is preferably placed in the gastric cardia, abutting the gastroesophageal junction. Where the patient is undergoing a focal ablation of any residual disease, it is preferable to use the catheter system shown in FIG. 4b, as discussed below. In one embodiment, the positioning attachment must be separated from the ablation region by a distance of greater than 0 mm, preferably 1 mm and ideally 1 cm. In one embodiment, the size of the positioning device is in the range of 10 to 100 mm, preferably 20-40 mm, although one of ordinary skill in the art would appreciate that the precise dimensions are dependent on the size of the patient's esophagus.

The delivery of ablative agent 21 through the infusion port 12 is controlled by the microprocessor 15 coupled with the ablation device. The delivery of ablative agent is guided by predetermined programmatic instructions, depending on the tissue to be ablated and the depth of ablation required. In one embodiment, the target procedural temperature will need to be between −100 degrees Celsius and 200 degrees Celsius, preferably between 50 degrees Celsius and 75 degrees Celsius, as further shown in the dosimetery table below. In one embodiment, esophageal pressure should not to exceed 5 atm, and is preferably below 0.5 atm. In one embodiment, the target procedural temperature is achieved in less than 1 minute, preferably in less than 5 seconds, and is capable of being maintained for up to 10 minutes, preferably 1 to 10 seconds, and then cooled to body temperature. One of ordinary skill in the art would appreciate that the treatment can be repeated until the desired ablation effect is achieved.

Figure 3B:
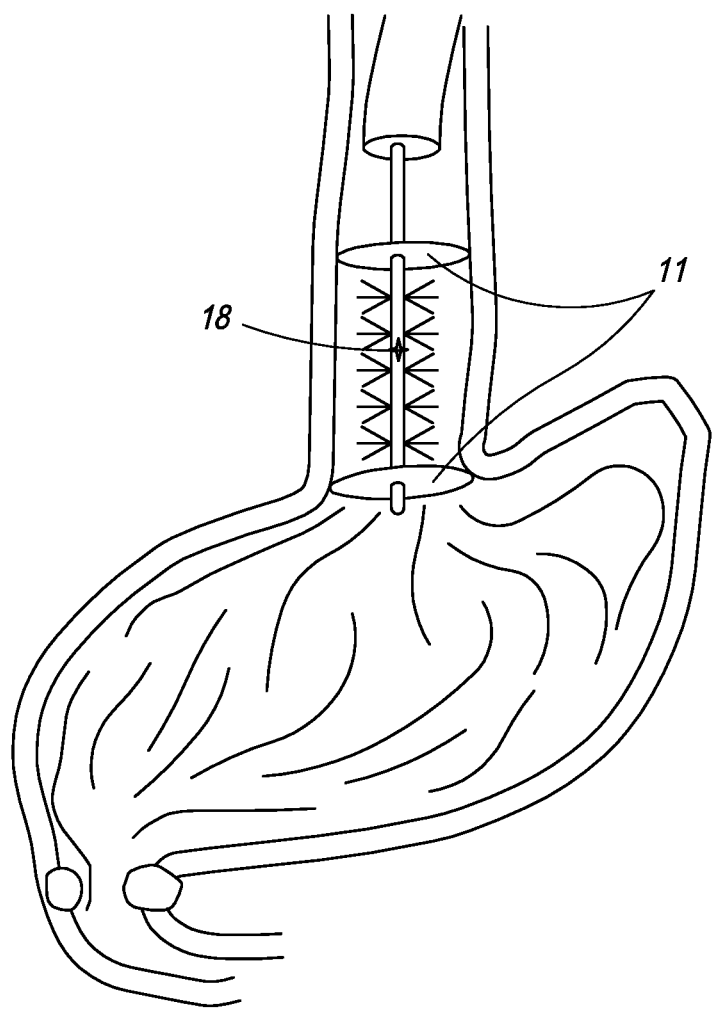
FIG. 3b. illustrates the ablation device placed in an upper gastrointestinal tract with Barrett esophagus to selectively ablate the Barrett tissue, in accordance with another embodiment of the present invention.

Optional sensor 17 monitors intraluminal parameters such as temperature and pressure and can increase or decrease the flow of ablative agent 21 through the infusion port 12 to obtain adequate heating or cooling, resulting in adequate ablation. The sensor 17 monitors intraluminal parameters such as temperature and pressure and can increase or decrease the removal of ablative agent 21 through the optional suction port 13 to obtain adequate heating or cooling resulting in adequate ablation of Barrett esophagus 31. FIG. 3b illustrates the ablation device placed in an upper gastrointestinal tract with Barrett esophagus to selectively ablate the Barrett tissue, in accordance with another embodiment of the present invention. As illustrated in FIG. 3b, the positioning device 11 is a wire mesh disc. In one embodiment, the positioning attachment must be separated from the ablation region by a distance of greater than 0 mm, preferably 1 mm and ideally 1 cm. In one embodiment, the positioning attachment is removably affixed to the cardia or EG junction (for the distal attachment) or in the esophagus by a distance of greater than 0.1 mm, preferably around 1 cm, above the proximal most extent of the Barrett tissue (for the proximal attachment).

FIG. 3b is another embodiment of the Barrett ablation device where the positioning element 11 is a wire mesh disc. The wire mesh may have optional insulated membrane to prevent the escape of the ablative agent. In the current embodiment, two wire mesh discs are used to center the ablation catheter in the esophagus. The distance between the two discs is determined by the length of the tissue to ablated which, in this case, would be the length of the Barrett esophagus. Optional infrared, electromagnetic, acoustic or radiofrequency energy emitter and sensor 18 are incorporated to measures the diameter of the esophagus.

Figure 3C:
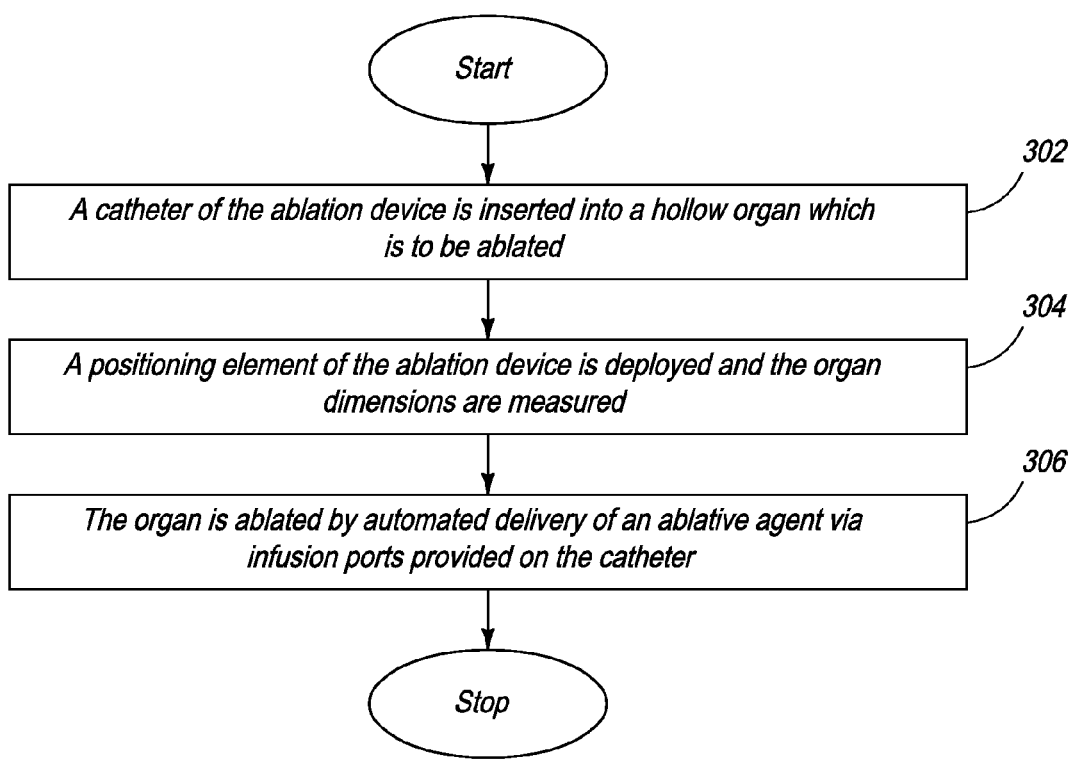
FIG. 3c is a flowchart illustrating the basic procedural steps for using the ablation device, in accordance with an embodiment of the present invention.

FIG. 3c is a flowchart illustrating the basic procedural steps for using the ablation device, in accordance with an embodiment of the present invention. At step 302, a catheter of the ablation device is inserted into a hollow organ which is to be ablated. For example, in order to perform ablation in a Barrett esophagus of a patient the catheter is inserted into the Barrett esophagus via the esophagus of the patient.

At step 304, a positioning element of the ablation device is deployed. In an embodiment, where the positioning element is a balloon, the balloon is inflated in order to position the ablation device at a known fixed distance from the tissue to be ablated. The diameter of the hollow organ may either be predetermined by using radiological tests such as barium X-rays or computer tomography (CT) scan, or by using pressure volume cycle, i.e by determining volume needed to raise pressure to a fixed level (say 1 atm) in a fixed volume balloon. In another embodiment, where the positioning device is disc shaped, circumferential rings are provided in order to visually communicate to an operating physician the diameter of the hollow organ. In various embodiments of the present invention, the positioning device enables centering of the catheter of the ablation device in a non-cylindrical body cavity, and the volume of the cavity is measured by the length of catheter or a uterine sound.

Optional, one or more, infrared, electromagnetic, acoustic or radiofrequency energy emitter and sensor can be used to measure the dimensions of the hollow organ. The infrared, electromagnetic, acoustic or radiofrequency energy is emitted from the emitter and is reflected back from the tissue to a detector in the emitter. The reflected data can be used to determine the dimension of the hollow cavity. The measurement can be performed at one or multiple points to get an accurate estimate of the dimension of the hollow organ. The data from multiple points can also be used to create a topographic representation of the hollow organ or to calculate the volume of the hollow organ.

In one embodiment, the positioning attachment must be separated from the ports by a distance of 0 mm or greater, preferably greater than 0.1 mm, and more preferably 1 cm. The size of the positioning device depends on the hollow organ being ablated and ranges from 1 mm to 10 cm. In one embodiment, the diameter of the positioning element is between 0.01 mm and 100 mm. In one embodiment, the first positioning element comprises a circular body with a diameter between 0.01 mm and 10 cm.

At step 306, the organ is ablated by automated delivery of an ablative agent such as steam via infusion ports provided on the catheter. The delivery of the ablative agent through the infusion ports is controlled by a microprocessor coupled with the ablation device. The delivery of ablative agent is guided by predetermined programmatic instructions depending on the tissue to be ablated and the depth of ablation required. In an embodiment of the present invention where the ablative agent is steam, the dose of the ablative agent is determined by conducting dosimetery study to determine the dose to ablate endometrial tissue. The variable that enables determination of total dose of ablative agent is the volume (or mass) of the tissue to be treated which is calculated by using the length of the catheter and diameter of the organ (for cylindrical organs). The determined dose of ablative agent is then delivered using micro-processor controlled steam generator.

In one embodiment, the dose is provided by first determining what the disorder being treated is and what the desired tissue effect is, and then finding the corresponding temperature, as shown in the tables below.

| Temp | Tissue Effect |
|---|---|
| 37-40 | No significant tissue effect |
| 41-44 | Reversible cell damage in few hours |
| 45-49 | Irreversible cell damage at shorter intervals |
| 50-69 | Irreversible cell damage -ablation necrosis at shorter intervals |
| 70 | Threshold temp for tissue shrinkage, H-bond breakage |
| 70-99 | Coagulation and Hemostasis |
| 100-200 | Desiccation and Carbonization of tissue |
| >200 | Charring of tissue glucose |

| Disorder | Max. Temp |
|---|---|
| ENT/Pulmonary | |
| Nasal Polyp | 60-80 C. |
| Turbinectomy | 70-85 C. |
| Bullous Disease | 70-85 C. |
| Lung Reduction | 70-85 C. |
| Genitourinary | |
| Uterine Menorrhagia | 80-90 C. |
| Endometriosis | 80-90 C. |
| Uterine Fibroids | 90-100 C. |
| Benign Prostatic Hypertrophy | 90-100 C. |
| Gastroenterology | |
| Barrett Esophagus | 60-75 C. |
| Esophageal Dysplasia | 60-80 C. |
| Vascular GI Disorders | 55-75 C. |
| Flat Polyps | 60-80 C. |

In addition, the depth of ablation desired determines the holding time at the maximum temperature. For superficial ablation (Barrett), the holding time at the maximum temperature is very short (flash burn) and does not allow for heat to transfer to the deeper layers. This will prevent damage to deeper normal tissue and hence prevention patient discomfort and complication. For deeper tissue ablation, the holding time at the maximum temperature will be longer, thereby allowing the heat to percolate deeper.

Figure 4A:
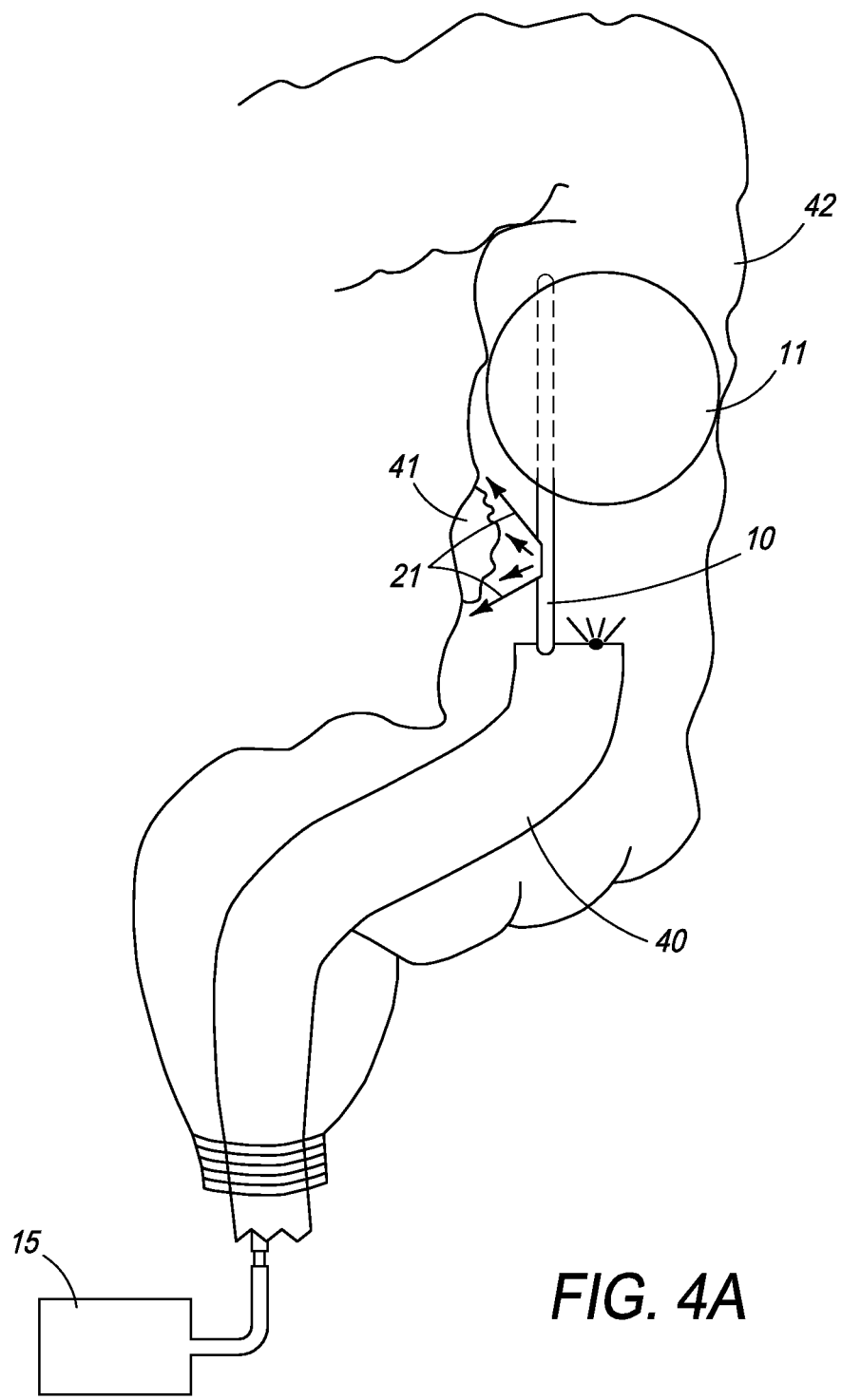
FIG. 4a illustrates the ablation device placed in a colon to ablate a flat colon polyp, in accordance with an embodiment of the present invention.

FIG. 4a illustrates the ablation device placed in a colon to ablate a flat colon polyp, in accordance with an embodiment of the present invention. The ablation catheter 10 is passed through a colonoscope 40. The positioning device 11 is placed proximal to a flat colonic polyp 41 which is to be ablated, in the normal colon 42. The positioning device 11 is one of an inflatable balloon, a wire mesh disc with or without an insulated membrane covering the disc, a cone shaped attachment, a ring shaped attachment or a freeform attachment designed to fit the colonic lumen. The positioning device 11 has the catheter 10 located toward the periphery of the positioning device 11 placing it closer to the polyp 41 targeted for non-circumferential ablation. Hence, the positioning device 11 fixes the catheter to the colon 42 at a predetermined distance from the polyp 41 for uniform and focused delivery of the ablative agent 21. The delivery of ablative agent 21 through the infusion port 12 is controlled by the microprocessor 15 attached to the ablation device and depends on tissue and the depth of ablation required. The delivery of ablative agent 21 is guided by predetermined programmatic instructions depending on the tissue to be ablated and the area and depth of ablation required. The ablation device allows for focal ablation of diseased polyp mucosa without damaging the normal colonic mucosa located away from the catheter ports.

In one embodiment, the positioning attachment must be separated from the ablation region by a distance of greater than 0.1 mm, ideally more than 5 mm. In one embodiment, the positioning element is proximal to the colon polyp. For this application, the embodiment shown in FIG. 4b would be preferred.

Figure 4B:
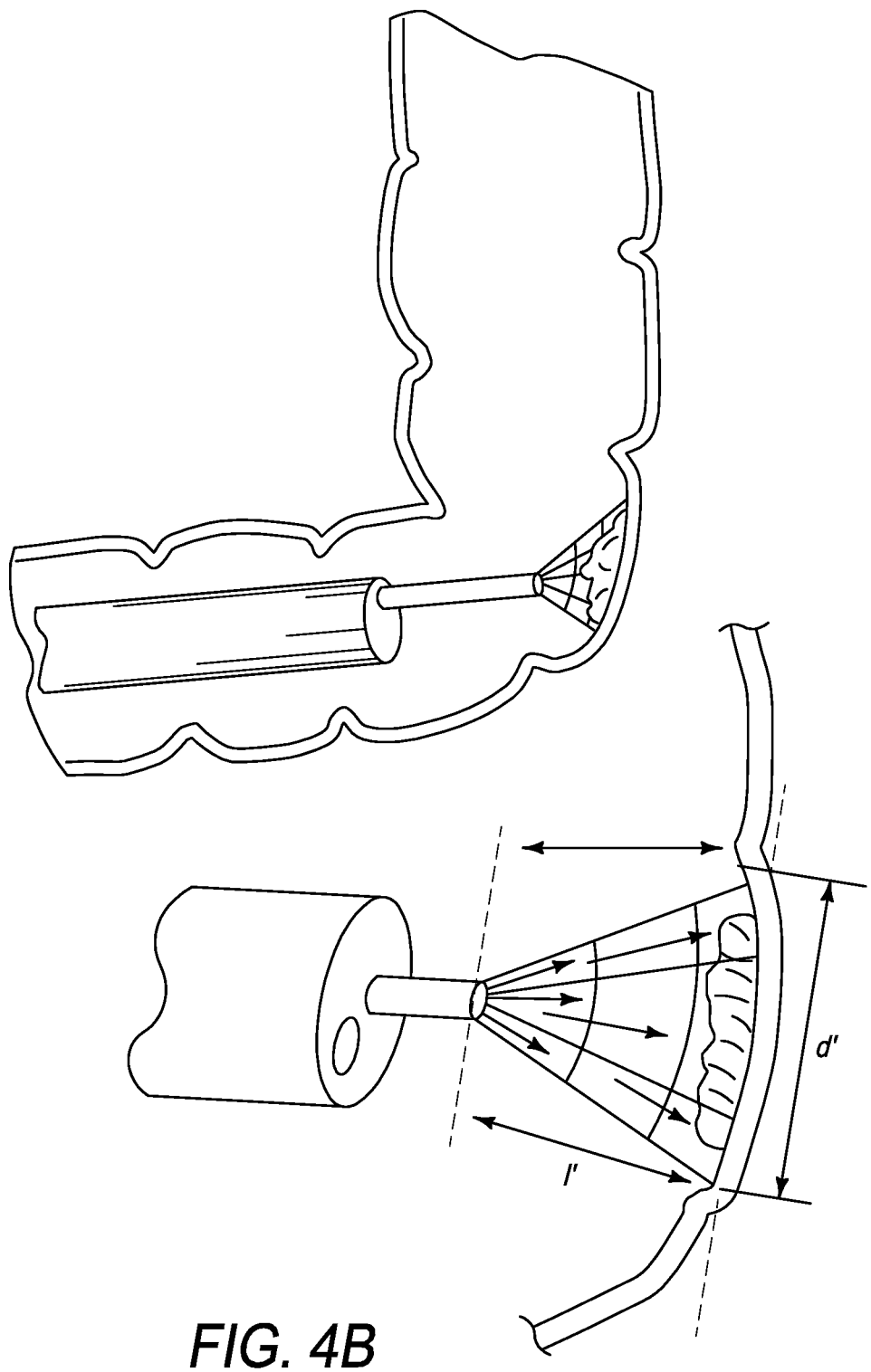
FIG. 4b illustrates the ablation device placed in a colon to ablate a flat colon polyp, in accordance with another embodiment of the present invention.

FIG. 4b illustrates the ablation device placed in a colon to ablate a flat colon polyp, in accordance with another embodiment of the present invention. As illustrated in FIG. 4b, the positioning device is a conical attachment at the tip of the catheter. The conical attachment has a known length 'l' and diameter 'd' that is used to calculate the amount of thermal energy needed to ablate the flat colon polyp. In one embodiment, the positioning attachment must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the polyp and can be between 1 mm and 10 cm, preferably 1 to 5 cm. This embodiment can also be used to ablate residual neoplastic tissue at the edges after endoscopic snare resection of a large sessile colon polyp.

Figure 5D:
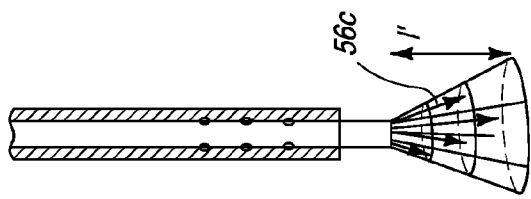
FIG. 5d illustrates the ablation device with a conical positioning element, in accordance with an embodiment of the present invention.
Figure 5C:
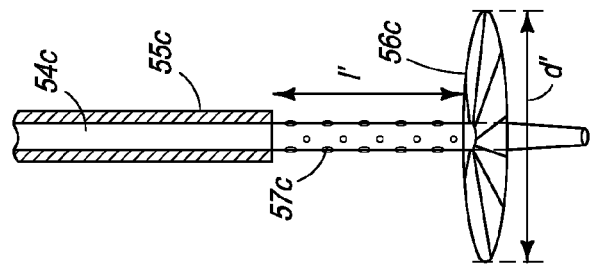
FIG. 5c illustrates a completely deployed positioning device, in accordance with an embodiment of the present invention.
Figure 5E:
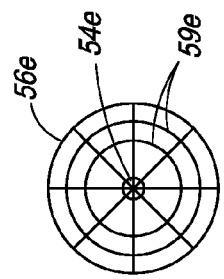
FIG. 5e illustrates the ablation device with a disc shaped positioning element, in accordance with an embodiment of the present invention.
Figure 5B:
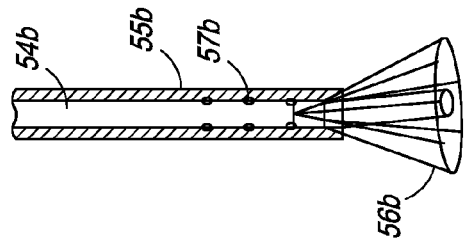
FIG. 5b illustrates a partially deployed positioning device, in accordance with an embodiment of the present invention.
Figure 5A:
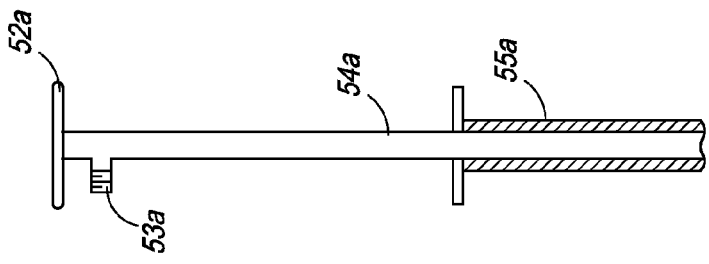
FIG. 5a illustrates the ablation device with a coaxial catheter design, in accordance with an embodiment of the present invention.

FIG. 5a illustrates the ablation device with a coaxial catheter design, in accordance with an embodiment of the present invention. The coaxial design has a handle 52a, an infusion port 53a, an inner sheath 54a and an outer sheath 55a. The outer sheath 55a is used to constrain the positioning device 56a in the closed position and encompasses ports 57a. FIG. 5b shows a partially deployed positioning device 56b, with the ports 57b still within the outer sheath 55b. The positioning device 56b is partially deployed by pushing the catheter 54b out of sheath 55b.

FIG. 5c shows a completely deployed positioning device 56c. The infusion ports 57c are out of the sheath 55c. The length 'l' of the catheter 54c that contains the infusion port 57c and the diameter 'd' of the positioning element 56c are predetermined/known and are used to calculate the amount of thermal energy needed. FIG. 5d illustrates a conical design of the positioning element. The positioning element 56d is conical with a known length 'l' and diameter 'd' that is used to calculate the amount of thermal energy needed for ablation. FIG. 5e illustrates a disc shaped design of the positioning element 56e comprising circumferential rings 59e. The circumferential rings 59e are provided at a fixed predetermined distance and used to estimate the diameter of a hollow organ or hollow passage in a patient's body.

Figure 6:
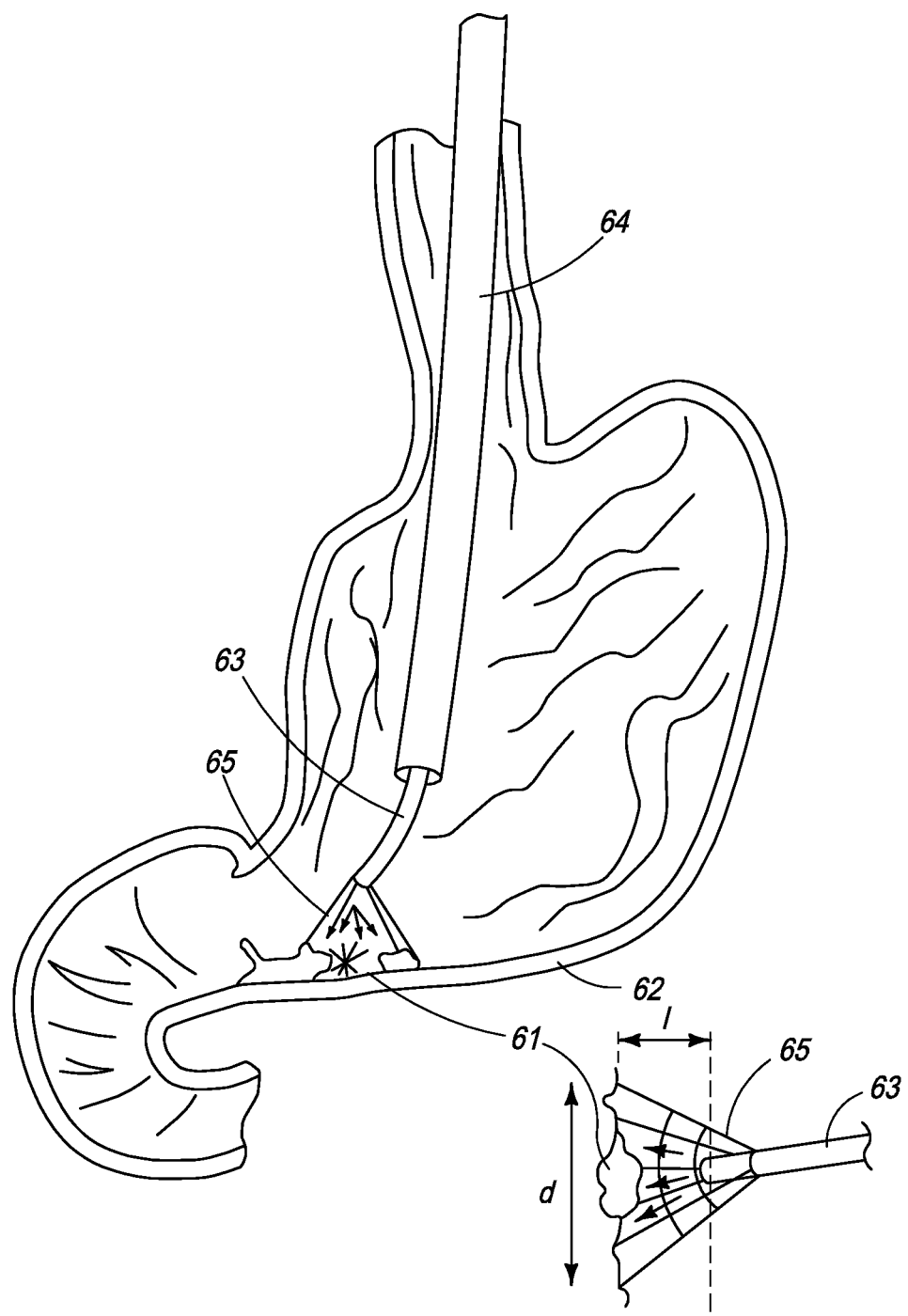
FIG. 6 illustrates an upper gastrointestinal tract with a bleeding vascular lesion being treated by the ablation device, in accordance with an embodiment of the present invention.

FIG. 6 illustrates an upper gastrointestinal tract with a bleeding vascular lesion being treated by the ablation device, in accordance with an embodiment of the present invention. The vascular lesion is a visible vessel 61 in the base of an ulcer 62. The ablation catheter 63 is passed though the channel of an endoscope 64. The conical positioning element 65 is placed over the visible vessel 61. The conical positioning element 65 has a known length 'l' and diameter 'd', which are used to calculate the amount of thermal energy needed for coagulation of the visible vessel to achieve hemostasis. The conical positioning element has an optional insulated membrane that prevents escape of thermal energy or vapor away from the disease site.

In one embodiment, the positioning attachment must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the lesion and can be between 1 mm and 10 cm, preferably 1 to 5 cm.

Figure 7:
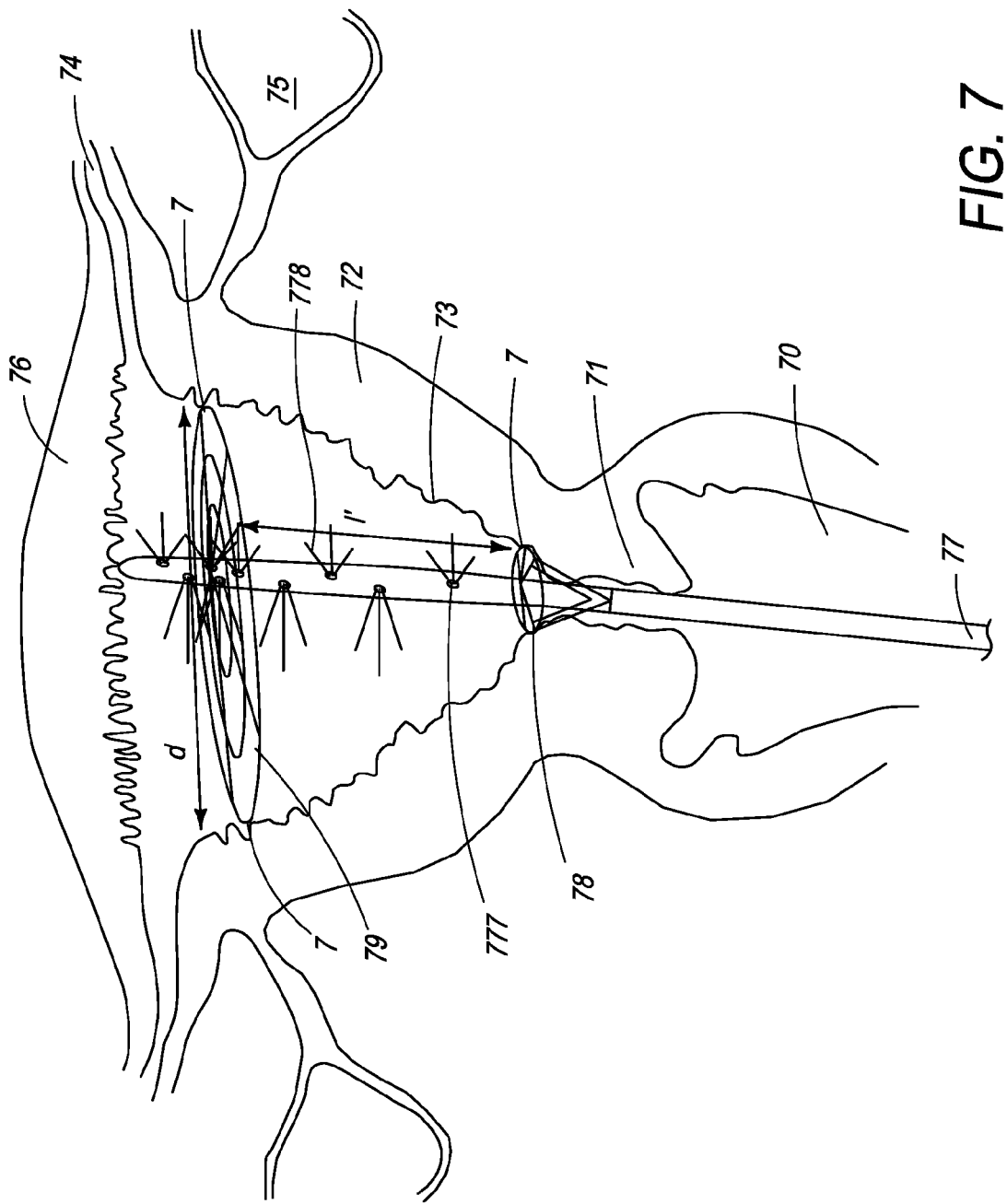
FIG. 7 illustrates endometrial ablation being performed in a female uterus by using the ablation device, in accordance with an embodiment of the present invention.

FIG. 7 illustrates endometrial ablation being performed in a female uterus by using the ablation device, in accordance with an embodiment of the present invention. A cross-section of the female genital tract comprising a vagina 70, a cervix 71, a uterus 72, an endometrium 73, fallopian tubes 74, ovaries 75 and the fundus of the uterus 76 is illustrated. A catheter 77 of the ablation device is inserted into the uterus 72 through the cervix 71. In an embodiment, the catheter 77 has two positioning elements, a conical positioning element 78 and a disc shaped positioning element 79. The positioning element 78 is conical with an insulated membrane covering the conical positioning element 78. The conical element 78 positions the catheter 77 in the center of the cervix 71 and the insulated membrane prevents the escape of thermal energy or ablative agent through the cervix 71. The second disc shaped positioning element 79 is deployed close to the fundus of the uterus 76 positioning the catheter 71 in the middle of the cavity. An ablative agent 778 is passed through infusion ports 777 for uniform delivery of the ablative agent 778 into the uterine cavity. Predetermined length "l" of the ablative segment of the catheter and diameter 'd' of the positioning element 79 allows for estimation of the cavity size and is used to calculate the amount of thermal energy needed to ablate the endometrial lining. Optional temperature sensors 7 deployed close to the endometrial surface are used to control the delivery of the ablative agent 778. Optional topographic mapping using multiple infrared, electromagnetic, acoustic or radiofrequency energy emitter and sensor can be used to define cavity size and shape in patients with irregular or deformed uterine cavity due to conditions such as fibroids.

In an embodiment, the ablative agent is steam which contracts on cooling. Steam turns to water which has a lower volume as compared to a cryogen that will expand or a hot fluid used in hydrothermal ablation whose volume stays constant. With both cryogens and hot fluids, increasing energy delivery is associated with increasing volume of the ablative agent which, in turn, requires mechanisms for removing the agent, otherwise the medical provider will run into complications. However, steam, on cooling, turn into water which occupies significantly less volume; therefore, increasing energy delivery is not associated with an increase in volume of the residual ablative agent, thereby eliminating the need for continued removal. This further decreases the risk of leakage of the thermal energy via the fallopian tubes 74 or the cervix 71, thus reducing any risk of thermal injury to adjacent healthy tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area. For endometrial ablation, 100% of the tissue does not need to be ablated to achieve the desired therapeutic effect.

In one embodiment, the preferred distal positioning attachment is an uncovered wire mesh that is positioned proximate to the mid body region. In one embodiment, the preferred proximal positioning device is a covered wire mesh that is pulled into the cervix, centers the device, and occludes the cervix. One or more such positioning devices may be helpful to compensate for the anatomical variations in the uterus. The proximal positioning device is preferably oval, with a long axis being between 0.1 mm and 10 cm (preferably 1 cm to 5 cm) and a short axis between 0.1 mm and 5 cm (preferably 0.5 cm to 1 cm). The distal positioning device is preferably circular with a diameter between 0.1 mm and 10 cm, preferably 1 cm to 5 cm.

Figure 8:
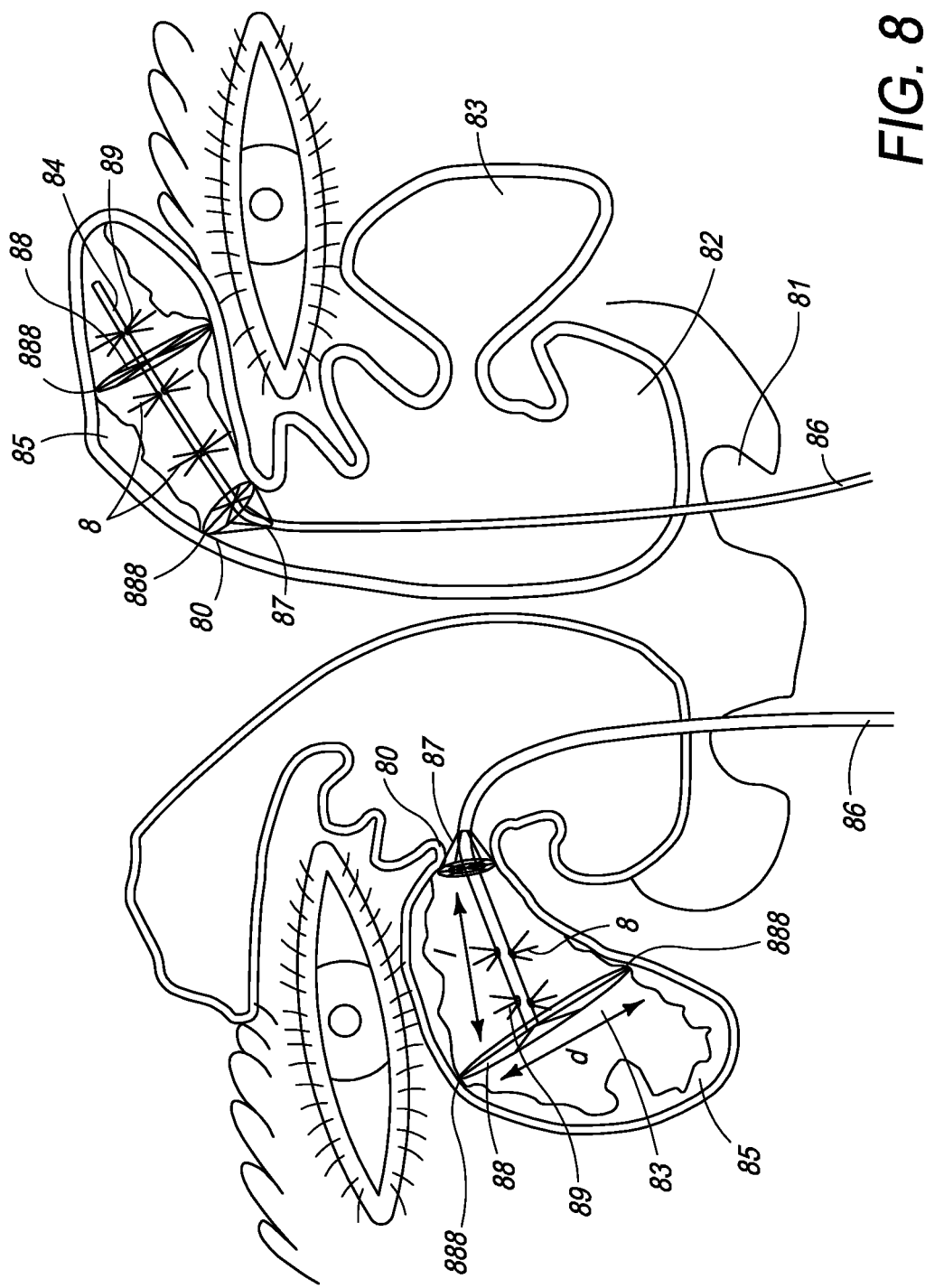
FIG. 8 illustrates sinus ablation being performed in a nasal passage by using the ablation device, in accordance with an embodiment of the present invention.

FIG. 8 illustrates sinus ablation being performed in a nasal passage by using the ablation device, in accordance with an embodiment of the present invention. A cross-section of the nasal passage and sinuses comprising nares 81, nasal passages 82, frontal sinus 83, ethemoid sinus 84, and diseased sinus epithelim 85 is illustrated. The catheter 86 is inserted into the frontal sinus 83 or the ethemoid sinus 84 through the nares 81 and nasal passages 82.

In an embodiment, the catheter 86 has two positioning elements, a conical positioning element 87 and a disc shaped positioning element 88. The positioning element 87 is conical and has an insulated membrane covering. The conical element 87 positions the catheter 86 in the center of the sinus opening 80 and the insulated membrane prevents the escape of thermal energy or ablative agent through the opening. The second disc shaped positioning element 88 is deployed in the frontal sinus cavity 83 or ethemoid sinus cavity 84, positioning the catheter 86 in the middle of either sinus cavity. The ablative agent 8 is passed through the infusion port 89 for uniform delivery of the ablative agent 8 into the sinus cavity. The predetermined length "l" of the ablative segment of the catheter and diameter 'd' of the positioning element 88 allows for estimation of the sinus cavity size and is used to calculate the amount of thermal energy needed to ablate the diseased sinus epithelium 85. Optional temperature sensors 888 are deployed close to the diseased sinus epithelium 85 to control the delivery of the ablative agent 8. In an embodiment, the ablative agent 8 is steam which contracts on cooling. This further decreases the risk of leakage of the thermal energy thus reducing any risk of thermal injury to adjacent healthy tissue. In one embodiment, the dimensional ranges of the positioning elements are similar to those in the endometrial application, with preferred maximum ranges being half thereof. Optional topographic mapping using multiple infrared, electromagnetic, acoustic or radiofrequency energy emitter and sensor can be used to define cavity size and shape in patients with irregular or deformed nasal cavity due to conditions such as nasal polyps.

Figure 9:
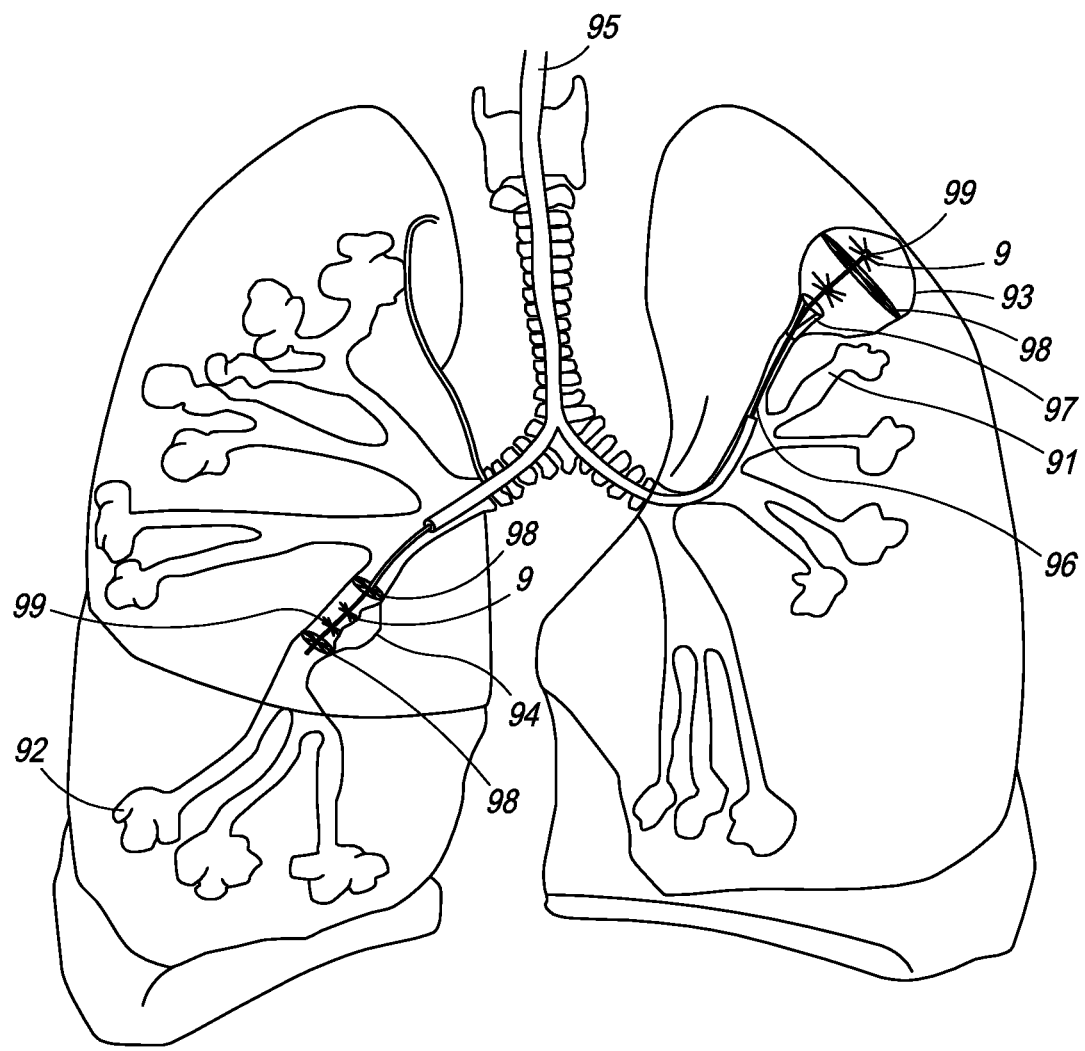
FIG. 9 illustrates bronchial and bullous ablation being performed in a pulmonary system by using the ablation device, in accordance with an embodiment of the present invention.

FIG. 9 illustrates bronchial and bullous ablation being performed in a pulmonary system by using the ablation device, in accordance with an embodiment of the present invention. A cross-section of the pulmonary system comprising bronchus 91, normal alveolus 92, bullous lesion 93, and a bronchial neoplasm 94 is illustrated.

In one embodiment, the catheter 96 is inserted through the channel of a bronchoscope 95 into the bronchus 91 and advanced into a bullous lesion 93. The catheter 96 has two positioning elements, a conical positioning element 97 and a disc shaped positioning element 98. The positioning element 97 is conical having an insulated membrane covering. The conical element 97 positions the catheter 96 in the center of the bronchus 91 and the insulated membrane prevents the escape of thermal energy or ablative agent through the opening into the normal bronchus. The second disc shaped positioning element 98 is deployed in the bullous cavity 93 positioning the catheter 96 in the middle of the bullous cavity 93. An ablative agent 9 is passed through the infusion port 99 for uniform delivery into the sinus cavity. Predetermined length "l" of the ablative segment of the catheter 96 and diameter 'd' of the positioning element 98 allow for estimation of the bullous cavity size and is used to calculate the amount of thermal energy needed to ablate the diseased bullous cavity 93. Optionally the size of the cavity can be calculated from radiological evaluation using a chest CAT scan or MRI. Optional temperature sensors are deployed close to the surface of the bullous cavity 93 to control the delivery of the ablative agent 9. In an embodiment, the ablative agent is steam which contracts on cooling. This further decreases the risk of leakage of the thermal energy into the normal bronchus thus reducing any risk of thermal injury to adjacent normal tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area.

In one embodiment, there are preferably two positioning attachments. In another embodiment, the endoscope is used as one fixation point with one positioning element. The positioning device is between 0.1 mm and 5 cm (preferably 1 mm to 2 cm). The distal positioning device is preferably circular with a diameter between 0.1 mm and 10 cm, preferably 1 cm to 5 cm.

In another embodiment for the ablation of a bronchial neoplasm 94, the catheter 96 is inserted through the channel of a bronchoscope 95 into the bronchus 91 and advanced across the bronchial neoplasm 94. The positioning element 98 is disc shaped having an insulated membrane covering. The positioning element 98 positions the catheter in the center of the bronchus 91 and the insulated membrane prevents the escape of thermal energy or ablative agent through the opening into the normal bronchus. The ablative agent 9 is passed through the infusion port 99 in a non-circumferential pattern for uniform delivery of the ablative agent to the bronchial neoplasm 94. The predetermined length "l" of the ablative segment of the catheter and diameter 'd' of the positioning element 98 are used to calculate the amount of thermal energy needed to ablate the bronchial neoplasm 94.

Figure 10:
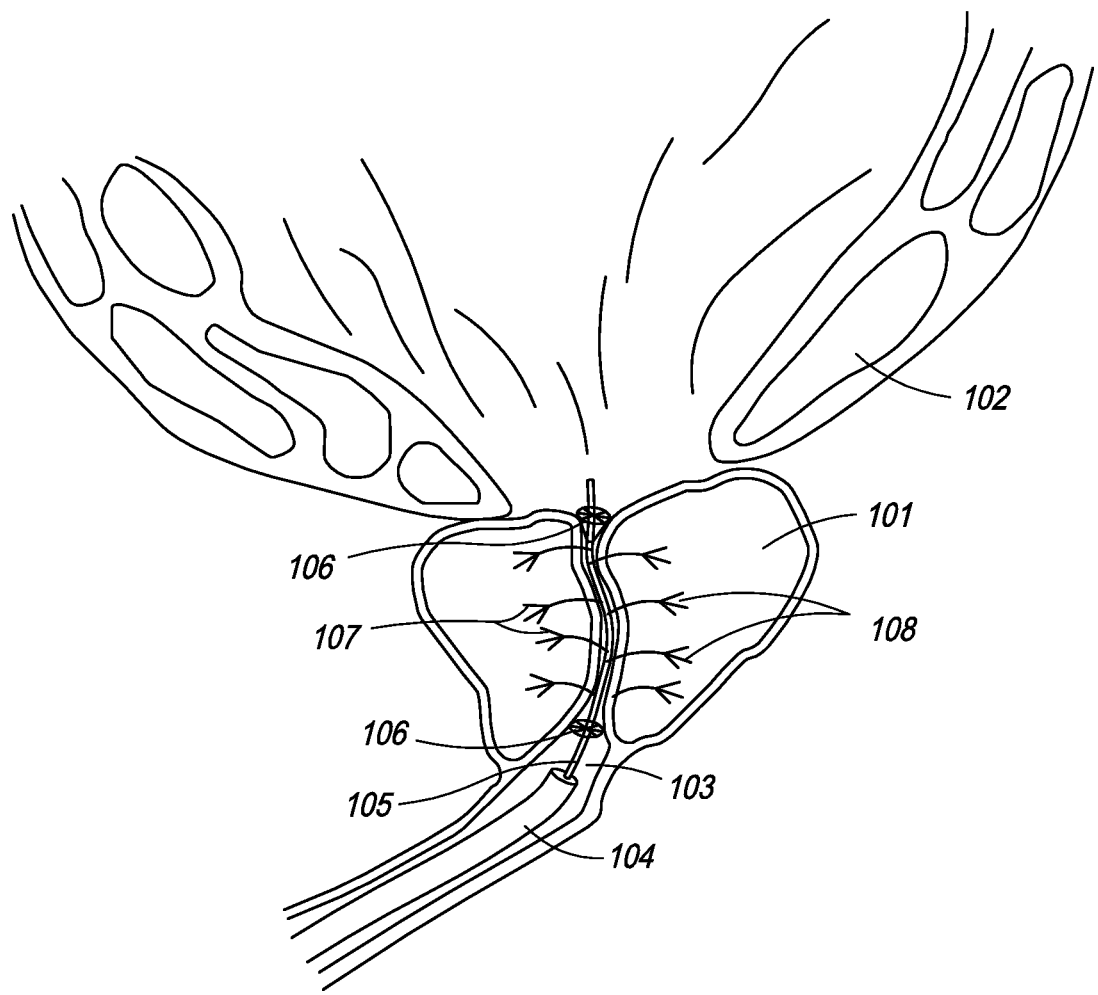
FIG. 10 illustrates prostate ablation being performed on an enlarged prostrate in a male urinary system by using the device, in accordance with an embodiment of the present invention.

FIG. 10 illustrates prostate ablation being performed on an enlarged prostrate in a male urinary system by using the device, in accordance with an embodiment of the present invention. A cross-section of a male genitourinary tract having an enlarged prostate 101, bladder 102, and urethra 103 is illustrated. The urethra 103 is compressed by the enlarged prostate 101. The ablation catheter 105 is passed through the cystoscope 104 positioned in the urethra 103 distal to the obstruction. The positioning elements 106 are deployed to center the catheter in the urethra 103 and insulated needles 107 are passed to pierce the prostate 101. The vapor ablative agent 108 is passed through the insulated needles 107 thus causing ablation of the diseased prostatic tissue resulting in shrinkage of the prostate.

In one embodiment, the positioning attachment must be separated from the ablation region by a distance of greater than 0.1 mm, preferably 1 mm to 5 mm and no more than 2 cm. In another embodiment, the positioning attachment can be deployed in the bladder and pulled back into the urethral opening/neck of the bladder thus fixing the catheter. In one embodiment, the positioning device is between 0.1 mm and 10 cm.

Figure 11:
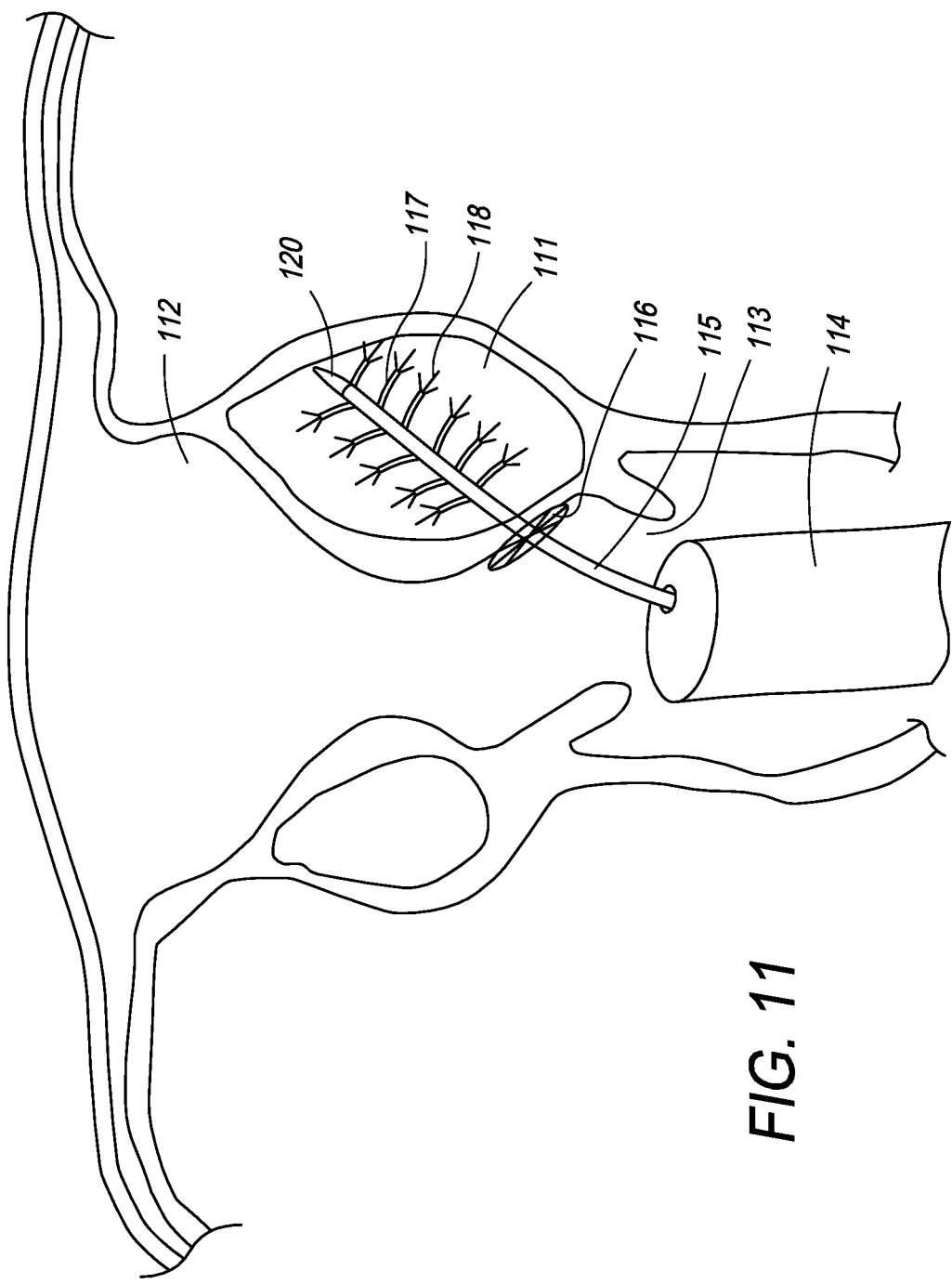
FIG. 11 illustrates fibroid ablation being performed in a female uterus by using the ablation device, in accordance with an embodiment of the present invention.

FIG. 11 illustrates fibroid ablation being performed in a female uterus by using the ablation device, in accordance with an embodiment of the present invention. A cross-section of a female genitourinary tract comprising a uterine fibroid 111, uterus 112, and cervix 113 is illustrated. The ablation catheter 115 is passed through the hysteroscope 114 positioned in the uterus distal to the fibroid 111. The ablation catheter 115 has a puncturing tip 120 that helps puncture into the fibroid 111. The positioning elements 116 are deployed to center the catheter in the fibroid and insulated needles 117 are passed to pierce the fibroid tissue 111. The vapor ablative agent 118 is passed through the needles 117 thus causing ablation of the uterine fibroid 111 resulting in shrinkage of the fibroid.

Figure 12:
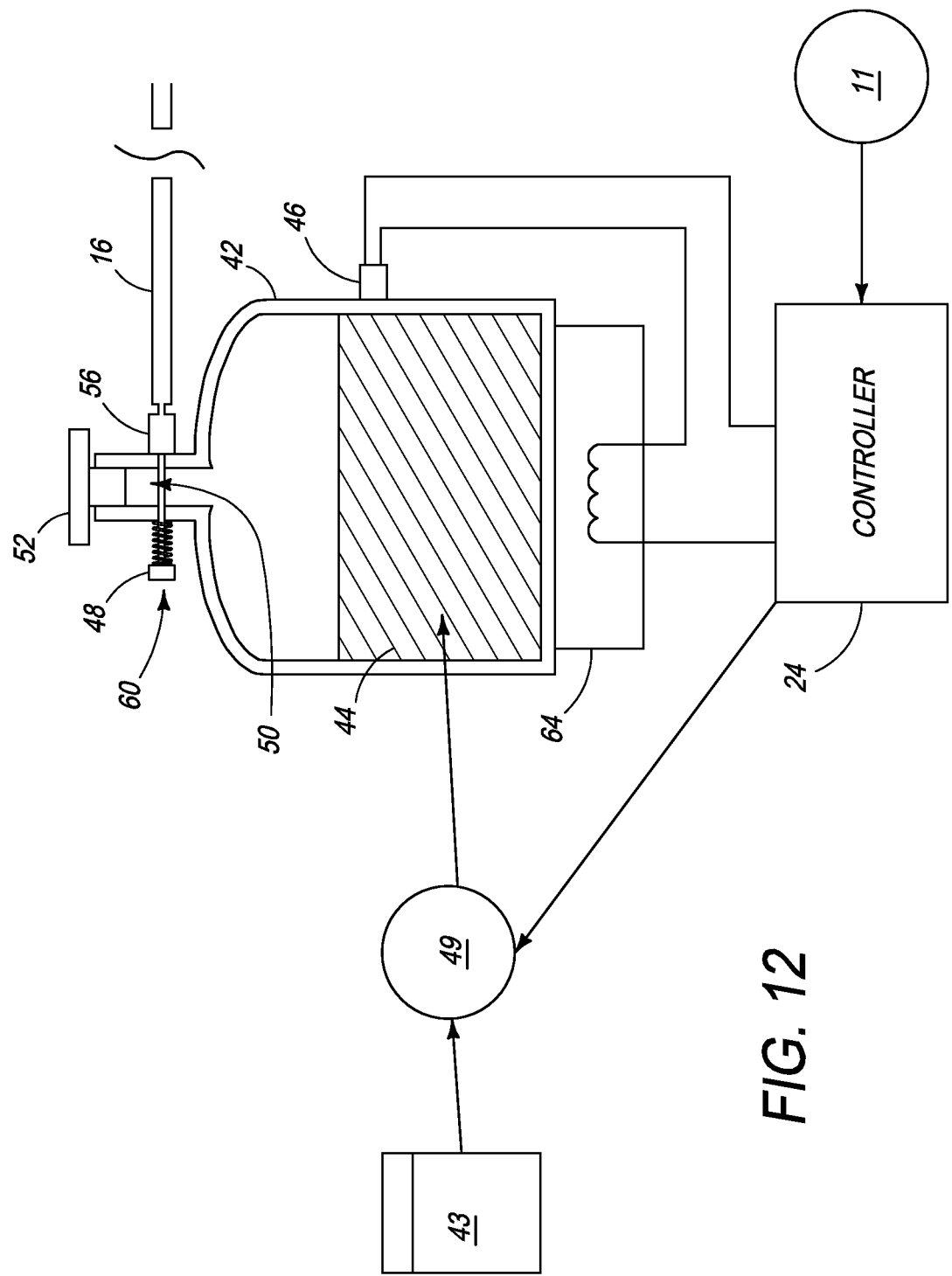
FIG. 12 illustrates a vapor delivery system using an RF heater for supplying vapor to the ablation device, in accordance with an embodiment of the present invention.

FIG. 12 illustrates a vapor delivery system using an RF heater for supplying vapor to the ablation device, in accordance with an embodiment of the present invention. In an embodiment, the vapor is used as an ablative agent in conjunction with the ablation device described in the present invention. RF heater 64 is located proximate a pressure vessel 42 containing a liquid 44. RF heater 64 heats vessel 42, in turn heating the liquid 44. The liquid 44 heats up and begins to evaporate causing an increase in pressure inside the vessel 42. The pressure inside vessel 42 can be kept fairly constant by providing a thermal switch 46 that controls resistive heater 64. Once, the temperature of the liquid 44 reaches a predetermined temperature, the thermal switch 46 shuts off RF heater 64. The vapor created in pressure vessel 42 may be released via a control valve 50. As the vapor exits vessel 42, a pressure drop is created in the vessel resulting in a reduction in temperature. The reduction of temperature is measured by thermal switch 46, and RF heater 64 is turned back on to heat liquid 44. In one embodiment, the target temperature of vessel 42 may be set to approximately 108° C., providing a continuous supply of vapor. As the vapor is released, it undergoes a pressure drop, which reduces the temperature of the vapor to a range of approximately 90-100° C. As liquid 44 in vessel 42 evaporates and the vapor exits vessel 42, the amount of liquid 44 slowly diminishes. The vessel 42 is optionally connected to reservoir 43 containing liquid 44 via a pump 49 which can be turned on by the controller 24 upon sensing a fall in pressure or temperature in vessel 42 delivering additional liquid 44 to the vessel 42.

Vapor delivery catheter 16 is connected to vessel 42 via a fluid connector 56. When control valve 50 is open, vessel 42 is in fluid communication with delivery catheter 16 via connector 56. Control switch 60 may serve to turn vapor delivery on and off via actuator 48. For example, control switch 60 may physically open and close the valve 50, via actuator 48, to control delivery of vapor stream from the vessel 42. Switch 60 may be configured to control other attributes of the vapor such as direction, flow, pressure, volume, spray diameter, or other parameters.

Instead of, or in addition to, physically controlling attributes of the vapor, switch 60 may electrically communicate with a controller 24. Controller 24 controls the RF heater 64, which in turn controls attributes of the vapor, in response to actuation of switch 60 by the operator. In addition, controller 24 may control valves temperature or pressure regulators associated with catheter 16 or vessel 42. A flow meter 52 may be used to measure the flow, pressure, or volume of vapor delivery via the catheter 16. The controller 24 controls the temperature and pressure in the vessel 42 and the time, rate, flow, volume of vapor flow through the control valve 50. These parameters are set by the operator 11. The pressure created in vessel 42, using the target temperature of 108° c., may be in the order of 25 pounds per square inch (psi) (1.72 bars).

Figure 13:
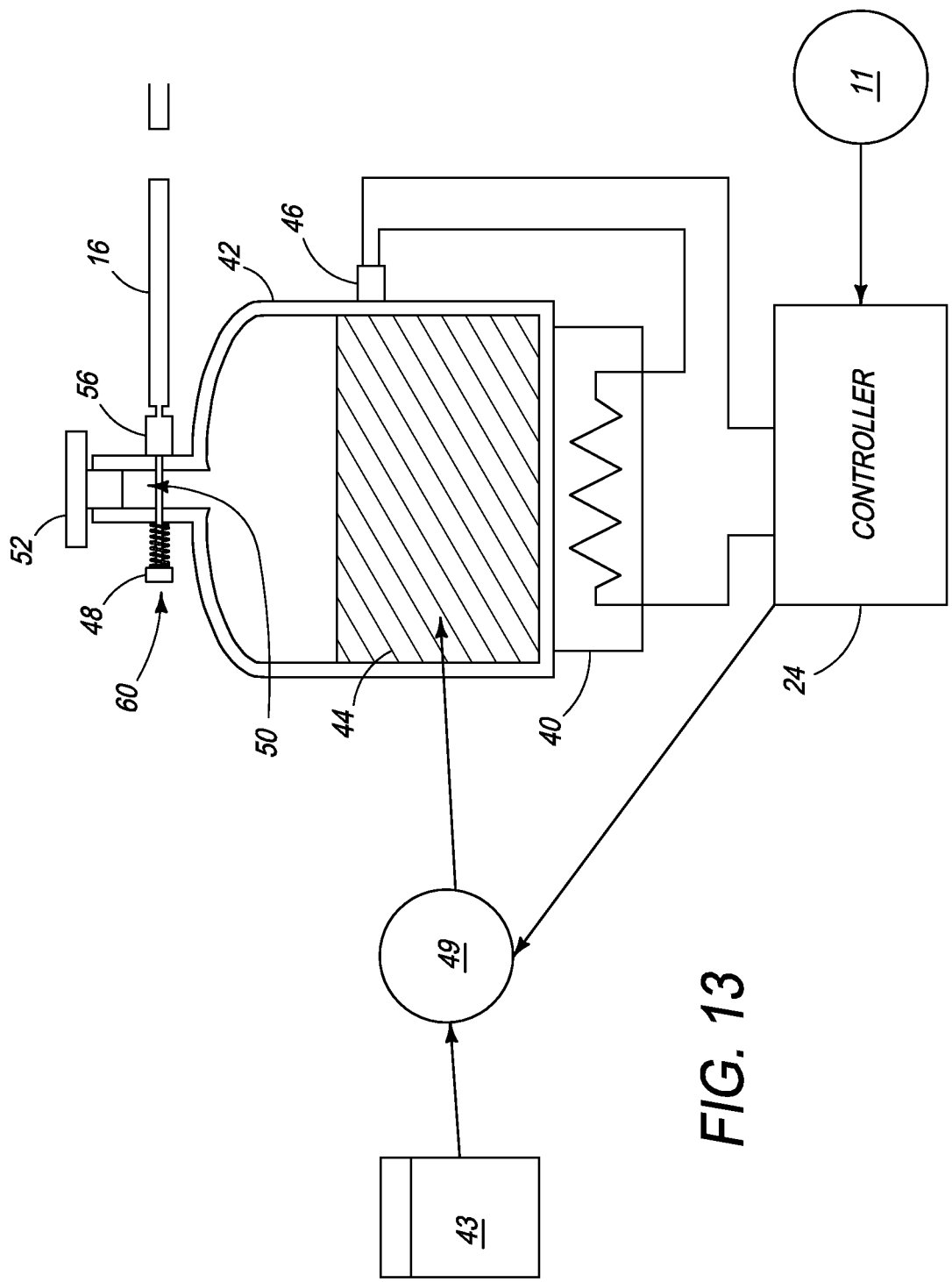
FIG. 13 illustrates a vapor delivery system using a resistive heater for supplying vapor to the ablation device, in accordance with an embodiment of the present invention.

FIG. 13 illustrates a vapor delivery system using a resistive heater for supplying vapor to the ablation device, in accordance with an embodiment of the present invention. In an embodiment, the generated vapor is used as an ablative agent in conjunction with the ablation device described in the present invention. Resistive heater 40 is located proximate a pressure vessel 42. Vessel 42 contains a liquid 44. Resistive heater 40 heats vessel 42, in turn heating liquid 44. Accordingly, liquid 44 heats and begins to evaporate. As liquid 44 begins to evaporate, the vapor inside vessel 42 causes an increase in pressure in the vessel. The pressure in vessel 42 can be kept fairly constant by providing a thermal switch 46 that controls resistive heater 40. When the temperature of liquid 44 reaches a predetermined temperature, thermal switch 46 shuts off resistive heater 40. The vapor created in pressure vessel 42 may be released via a control valve 50. As the vapor exits vessel 42, vessel 42 experiences a pressure drop. The pressure drop of vessel 42 results in a reduction of temperature. The reduction of temperature is measured by thermal switch 46, and resistive heater 40 is turned back on to heat liquid 44. In one embodiment, the target temperature of vessel 42 may be set to approximately 108° C., providing a continuous supply of vapor. As the vapor is released, it undergoes a pressure drop, which reduces the temperature of the vapor to a range of approximately 90-100° C. As liquid 44 in vessel 42 evaporates and the vapor exits vessel 42, the amount of liquid 44 slowly diminishes. The vessel 42 is connected to another vessel 43 containing liquid 44 via a pump 49 which can be turned on by the controller 24 upon sensing a fall in pressure or temperature in vessel 44 delivering additional liquid 44 to the vessel 42.

Vapor delivery catheter 16 is connected to vessel 42 via a fluid connector 56. When control valve 50 is open, vessel 42 is in fluid communication with delivery catheter 16 via connector 56. Control switch 60 may serve to turn vapor delivery on and off via actuator 48. For example, control switch 60 may physically open and close the valve 50, via actuator 48, to control delivery of vapor stream from the vessel 42. Switch 60 may be configured to control other attributes of the vapor such as direction, flow, pressure, volume, spray diameter, or other parameters. Instead of, or in addition to, physically controlling attributes of the vapor, switch 60 may electrically communicate with a controller 24. Controller 24 controls the resistive heater 40, which in turn controls attributes of the vapor, in response to actuation of switch 60 by the operator. In addition, controller 24 may control valves temperature or pressure regulators associated with catheter 16 or vessel 42. A flow meter 52 may be used to measure the flow, pressure, or volume of vapor delivery via the catheter 16. The controller 24 controls the temperature and pressure in the vessel 42 as well as time, rate, flow, volume of vapor flow through the control valve 50. These parameters are set by the operator 11. The pressure created in vessel 42, using the target temperature of 108° C., may be on the order of 25 pounds per square inch (psi) (1.72 bars).

The device and method of the present invention can be used to cause controlled focal or circumferential ablation of targeted tissue to varying depth in a manner in which complete healing with re-epithelialization can occur. The dose and manner of treatment can be adjusted based on the type of tissue and the depth of ablation needed. The ablation device can be used not only for the treatment of Barrett esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesion of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

We claim:

1. A device adapted to treat Barrett's esophagus in an esophagus of a patient by ablating esophageal tissue, comprising:
  a catheter having an outer sheath and an inner shaft through which an ablative agent can travel, wherein the outer sheath is positioned around the inner shaft and movable with respect to the inner shaft;
  a first positioning element attached to said inner shaft at a distal end of said inner shaft, wherein said first positioning element comprises an inflatable balloon configured to be positioned in a gastric cardia of the patient, thereby positioning the catheter at a fixed distance from the esophageal tissue to be ablated;
  an input port at a second position and in fluid communication with said inner shaft in order to receive said ablative agent wherein the inner shaft comprises one or more ports through which said ablative agent can be released out of said inner shaft, wherein each of said one or more ports is positioned between the input port and the distal end along and circumferentially around said inner shaft and separated from the inflatable balloon by a distance of at least 1 mm; and
  a controller programmed to determine an amount of thermal energy needed to ablate said esophageal tissue programmed to limit a maximum dose of said ablative agent based on a type of disorder being treated, wherein said type of disorder comprises Barrett's esophagus, and programmed to limit the amount of thermal energy delivered such that a pressure within the patient's esophagus does not exceed 5 atm.

2. The device of claim 1 wherein said device is configured to generate said pressure within the patient's esophagus and wherein said pressure within the patient's esophagus is equal to or less than 5 atm.

3. The device of claim 1 wherein the ablative agent has a temperature between 100 degrees Celsius and 200 degrees Celsius.

4. The device of claim 1 wherein said catheter further comprises a temperature sensor.

5. The device of claim 1 wherein said catheter further comprises a pressure sensor.

6. The device of claim 1 wherein a diameter of the first positioning element is between 0.01 mm and 100 mm.

7. The device of claim 1 wherein said first positioning element comprises a circular body with a diameter between 0.01 mm and 10 cm.

8. A device adapted to treat Barrett's esophagus in an esophagus of a patient by ablating esophageal tissue, comprising
  a catheter having a hollow inner shaft through which steam can be transported;
  a first positioning element attached to said catheter at a distal end of said catheter, wherein said first positioning element comprises an inflatable balloon configured to abut a gastroesophageal junction when placed in a gastric cardia;
  an input port at a second position and in fluid communication with said hollow inner shaft in order to receive said steam wherein the hollow inner shaft comprises a plurality of ports through which said steam can be released out of said hollow inner shaft, wherein each of said plurality of ports is positioned between the input port and the distal end along and circumferentially around said hollow inner shaft and separated from the inflatable balloon by a distance of at least 1 mm; and
  a controller programmed to determine an amount of thermal energy needed to ablate said esophageal tissue, programmed to limit a maximum dose of said steam based on a type of disorder being treated, wherein said type of disorder comprises Barrett's esophagus, and programmed to limit the amount of thermal energy delivered such that a pressure within the patient's esophagus does not exceed 5 atm.

9. The device of claim 7 further comprising a temperature sensor wherein said temperature sensor is used to control a release of said steam.

10. The device of claim 7 wherein said first positioning element is separated from each of said plurality of ports by a distance of up to 10 cm.

11. The device of claim 7 wherein a diameter of the first positioning element is between 10 mm and 100 mm.

12. A device adapted to treat Barrett's esophagus in an esophagus of a patient by ablating esophageal tissue, comprising
  a catheter having a hollow shaft through which steam can be transported;
  a first positioning element attached to said catheter at a distal end of said shaft, wherein said first positioning element comprises an inflatable balloon configured to abut the esophageal tissue;
  an input port at a second position and in fluid communication with said hollow shaft in order to receive said steam wherein the hollow shaft comprises one or more ports, through which said steam can be released out of said hollow shaft onto the esophageal tissue, wherein each of said one or more ports is positioned between the input port and the distal end along and circumferentially around said shaft and separated from the inflatable balloon by a distance of at least 1 mm; and
  a controller programmed to
    calculate an amount of thermal energy needed to ablate said esophageal tissue based, at least in part, on a volume of said first positioning element indicative of a distance to said esophageal tissue;
    limit a maximum dose of said steam based on a type of disorder being treated, wherein said type of disorder comprises Barrett's esophagus;
    determine a dimension of said esophageal tissue by using a pressure volume cycle to raise a pressure of the inflatable balloon to a predetermined level and thereby determine said volume of said first positioning element; and
    limit the amount of thermal energy delivered such that a pressure within the patient's esophagus does not exceed 5 atm.

13. The device of claim 12 further comprising a temperature sensor wherein said temperature sensor is used to control a release of said steam.

14. The device of claim 12 wherein a diameter of the first positioning element is 0.1 mm to 50 mm.

* * * * *